United States Patent
Isom et al.

(10) Patent No.: US 6,610,471 B1
(45) Date of Patent: Aug. 26, 2003

(54) METHODS AND COMPOSITIONS TO INVESTIGATE INFECTION BY HEPATITIS B VIRUS AND AGENTS TO PREVENT AND TREAT THE INFECTION

(75) Inventors: Harriet C. Isom, Hershey, PA (US); William E. Delaney, IV, San Bruno, CA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/600,731

(22) PCT Filed: Jan. 20, 1999

(86) PCT No.: PCT/US99/01153
§ 371 (c)(1),
(2), (4) Date: Sep. 5, 2000

(87) PCT Pub. No.: WO99/37821
PCT Pub. Date: Jul. 29, 1999

Related U.S. Application Data
(60) Provisional application No. 60/072,017, filed on Jan. 21, 1998.

(51) Int. Cl.[7] .......................... C12Q 1/70; G01N 33/576
(52) U.S. Cl. .......................... 435/5; 435/69.1; 435/370; 436/820
(58) Field of Search .......................... 435/5, 69.1, 370; 436/820

(56) References Cited

PUBLICATIONS

Guidotti et al., High–Level Hepatitis B Virus Replication in Transgenic Mice. Journal of Virology 69(10):6158–6169, 1995.*

Hofmann et al., Efficient gene transfer into human hepatocytes by baculovirus vectors. Proc. Natl. Acad. Sci. 92: 10099–10103, 1995.*

Menzo et al., Trans–Activation of Epidermal Growth Factor Receptor Gene by the Hepatitis B Virus X–Gene Product. Virology 196:878–882, 1993.*

* cited by examiner

*Primary Examiner*—Donna C. Wortman
(74) *Attorney, Agent, or Firm*—McKee, Voorhees & Sease, P.L.C.

(57) ABSTRACT

Methods and compositions that use the hepatitis B virus genome, and fragments or extensions, in a baculovirus vector, to develop anti-HBV agents and to drive high-level expression of a desired gene in a cell of hepatic origin.

11 Claims, 32 Drawing Sheets

(2 of 32 Drawing Sheet(s) Filed in Color)

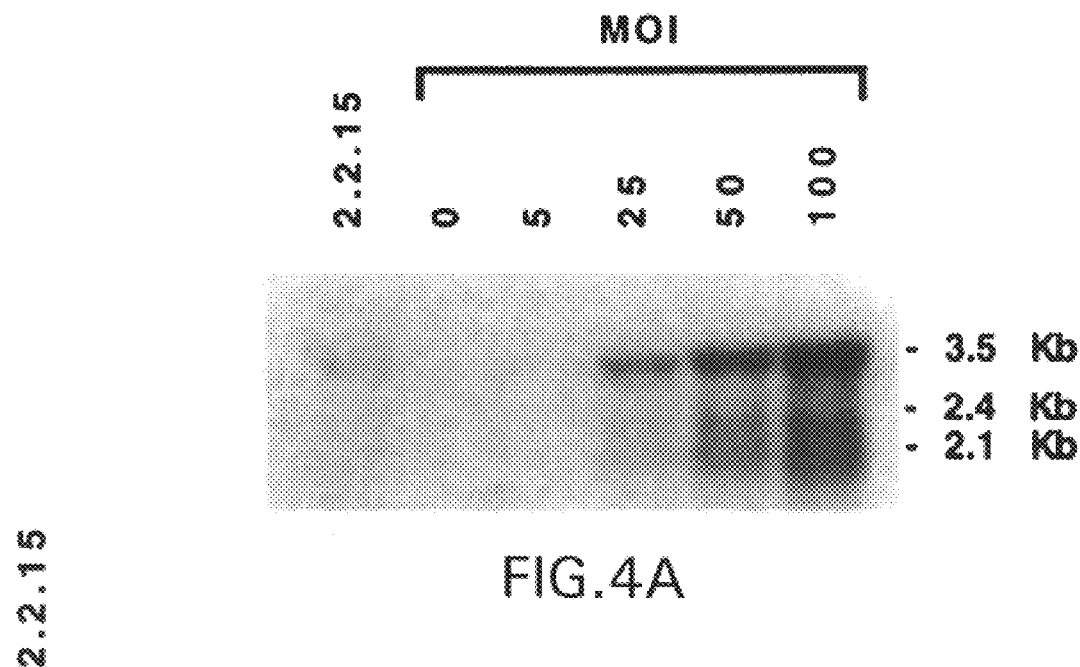
FIG.4A
FIG.4B
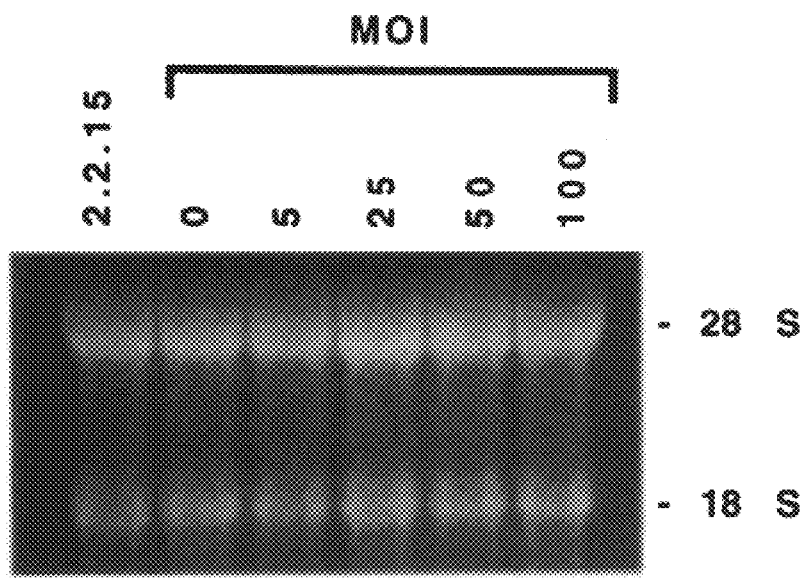
FIG.4C

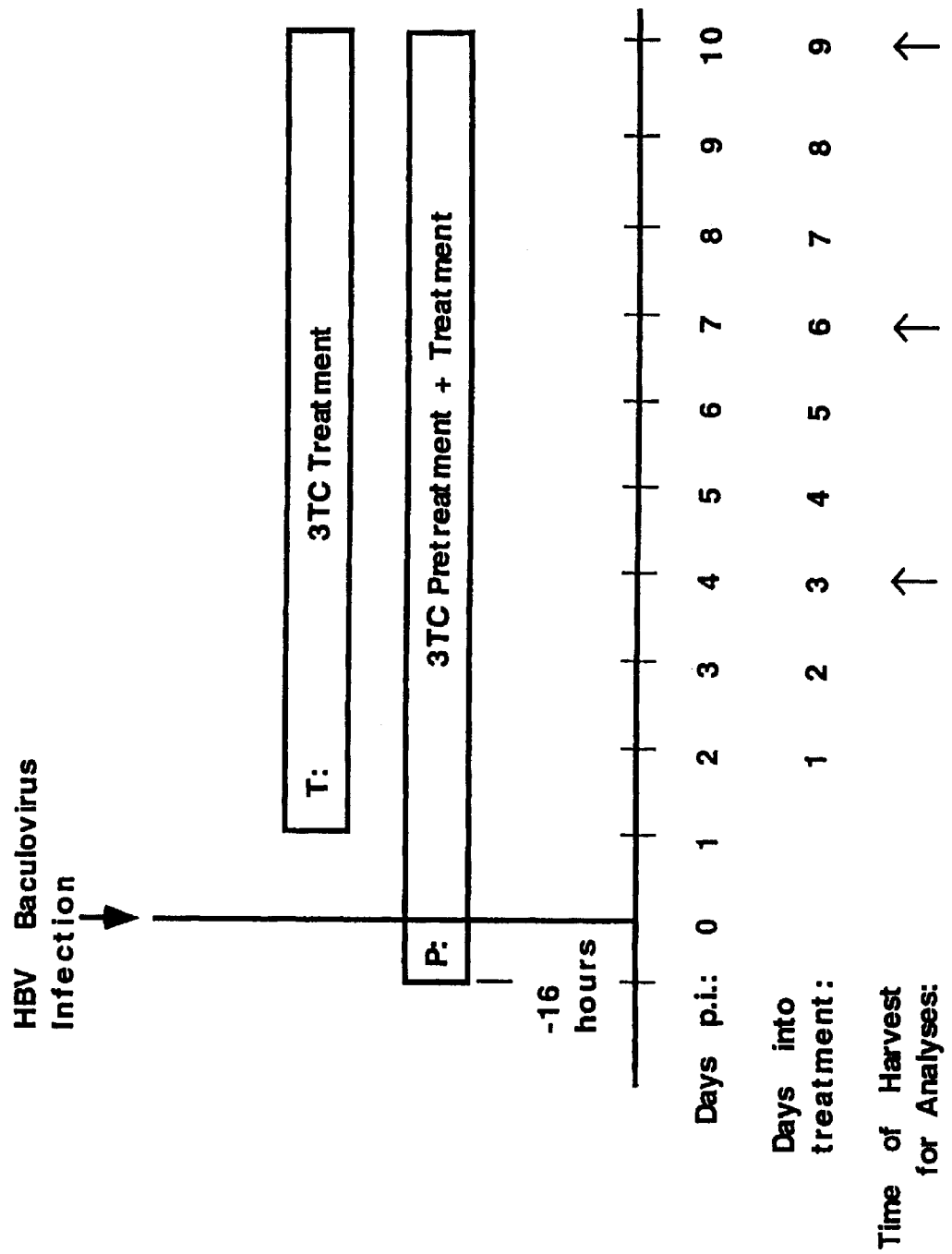

METHODS AND COMPOSITIONS TO INVESTIGATE INFECTION BY HEPATITIS B VIRUS AND AGENTS TO PREVENT AND TREAT THE INFECTION

RELATED APPLICATIONS

This application claims priority to U.S. Ser. No. 60/072017 filed Jan. 21, 1998, said application is incorporated by reference.

FEDERALLY SPONSORED RESEARCH OR DEVELOPMENT

Supported in part by research grants from the National Institutes of Health (CA73045 and CA23931).

BACKGROUND OF THE INVENTION

Methods and compositions are presented that use the hepatitis B virus genome, and fragments or extensions thereof, in a baculovirus vector, to develop anti-HBV agents.

Hepatitis B virus (HBV) is a small, double-stranded DNA virus and is the prototype of the hepadnavirus family. HBV is a human pathogen capable of causing both acute and chronic hepatitis. The World Health Organization currently estimates that 350 million people are chronically infected with HBV. Persistent HBV infection is also associated with an increased risk of cirrhosis and hepatocellular carcinoma.

Although vaccines against HBV exist, vaccination is expensive, not readily available in all parts of the world, and not all individuals develop immunity following vaccination. Therefore, there is a need to develop effective treatments for the millions of people who remain persistently infected, as well as the population who will become infected despite the existence of vaccines. Currently, the only approved therapy for chronic HBV infection is the cytokine interferon-α. Long-term studies on interferon-α therapy indicate that treatment can lead to the loss of circulating HBV antigens and improved survival rate but only in about 30% of patients receiving treatment. Interferon also must be administered by injection and can have undesirable side effects which limit dosage. Alternative treatment options which are effective alone or in combination with interferon-α must be explored.

Although much information has accumulated about HBV, knowledge of the virus is by no means complete, therefore prevention and treatment of HBV infections are deficient. Historically, major obstacles in the study of HBV have been the inability of the virus to infect cells in vitro, and the lack of animal model systems due to a strict virus-host range. Thus, many aspects of HBV biology have been unraveled by studying related hepadnaviruses, such as the duck hepatitis virus which is capable of in vitro infection, and the woodchuck hepatitis virus which allows for an in vivo study in an animal model system. The duck hepatitis virus and woodchuck hepatitis virus systems were instrumental in developing an understanding of the hepadnavirus lifecycle and remain valuable models for HBV infection. However, many significant differences exist between animal hepadnaviruses and the human HBV. For example, avian hepatitis viruses are lacking one of the four HBV open reading frames, and, therefore, do not encode one of the HBV gene products, the X protein. Transcriptional differences between woodchuck hepatitis virus and HBV have been reported. Therefore, animal models may not be reliable for the development of methods to prevent and treat human HBV-related diseases.

Transgenic mice have also been used to study HBV biology. For example, a 1.3 HBV construct was used to generate transgenic mice (Guidotti et al, 1995). The 1.3 HBV transgene was integrated into the mouse genome. These transgenic mouse lineages demonstrate high levels of HBV replication. However, covalently closed circular (CCC) DNA has not been detected as an intermediate in the HBV replication process in these transgenic mice.

Options currently available for studying the molecular mechanisms of HBV replication and the effects of antivirals and cytokines on HBV production within a cell background of human hepatic origin include using stably or transiently transfected cell lines.

Moving closer to predicting human responses to HBV, several HBV expressing cell lines have been established by transfecting viral DNA into liver-derived human cell lines and by selecting novel cell lines containing stably integrated HBV genomes. The most widely used cell lines are the HepG2 2.2.15 cell line (2.2.15) (Sells et al., 1987; 1988) derived from the HepG2 hepatoblastoma cell line (Knowles et al., 1980) and HB611 derived from the HuH6 hepatoma cell line. These and other cell lines have led to considerable progress in the study of HBV in vitro.

The 2.2.15 cell line which was derived from HepG2 cells and constitutively produces HBV has been used to evaluate in vitro inhibition of HBV replication by various nucleosides. Transient transfection of HepG2 cells have been used to ifs understand various aspects of HBV gene expression and replication at the molecular level. Some studies involve using greater than genome length HBV DNA sequences so that all HBV gene products can be produced. Transcription of linear HBV DNA requires a greater than unit length 3.2-kb HBV genome to produce the 3.5-kb pregenomic message which is required for replication. Others have concentrated on using HBV DNA sequences which encode restricted portions of the coding regions of the genome or enhancer or promoter sequences.

However, there are some inherent drawbacks which preclude the use of these cell lines in studying some aspects of HBV biology. Many HBV expressing cell lines were created using constructs that contain strong heterologous promoters proximal to the HBV genome. A "heterologous" promoter is one which is not a natural HBV promoter. The effect those promoters have on HBV transcription and replication is unclear, but effects could differ substantially from what occurs in a natural infection in vivo in which HBV gene expression is driven solely by endogenous HBV promoters.

Another reason cell lines may not be predictive of in vivo effects in humans, is that cell lines commonly used to study HBV contain multiple copies of integrated HBV DNA. Unlike retroviruses, which integrate viral DNA into the host genome, hepadnavirus genomes are not routinely integrated directly into the host genomes but, instead, are maintained in the nucleus of infected cells in vivo as a pool of episomal, covalently closed circular (CCC) DNA molecules. Although the integration of HBV DNA in human liver has been reported, it is not an obligatory part of the HBV lifecycle. HBV does not encode any machinery for integration into the host genome, and integration is not required for HBV replication. In addition, when integrated HBV DNA is found, it is frequently rearranged and is often transcriptionally silent. Because HBV expressing cell lines contain stably integrated HBV DNA, viral gene expression and replication is continuous; therefore, it is not possible to experimentally control the time or conditions under which these processes are initiated. Stable HBV expressing cell lines contain fixed numbers of integrated HBV genomes and, as such, HBV gene expression and replication levels cannot be regulated and are restricted to the number of integrated copies which each cell line contains. Consequently, it is not possible to study the effects of increasing or decreasing the copy number of integrated HBV genomes without retransfecting the cell line and/or selecting new cell lines.

There is a need, therefore, to develop model systems of HBV infection that more closely mimic actual clinical infections. To accomplish this, a means to initiate HBV replication within human cells in a manner simulating clinical infections is needed. Baculoviruses are a family of large double-stranded DNA viruses which infect and replicate in several types of invertebrate hosts. Baculoviruses have been widely used as insecticides and as agents for protein overexpression in insect cells. Recently, it has been reported that the baculovirus Autographa californica can be used as an effective vector for the transfer of reporter genes into mammalian hepatocytes. (Sanding et al., 1996; Boyce and Bucher, 1996; Hoffman et al., 1995) A requirement for baculovirus-mediated gene expression in hepatocytes appears to be the presence of a promoter which can function in mammalian cells to drive transcription of a target gene. Native baculovirus promoters appear to be ineffective in driving transcription in mammalian cells. There are several advantages of baculovirus-mediated transfer of HBV DNA into HepG2 cells compared to classical transfection procedures: 1) Significantly higher transfection levels (>10-fold higher) can be obtained. 2) Levels of HBV expression and replication can be precisely and reproducibly controlled simply by altering the multiplicity of infection (moi) with HBV baculovirus. 3) The infection procedure is rapid and requires a minimal manipulation of cultured cells. 4) Cultures of HepG2 cells can be superinfected with additional amounts of baculovirus to extend and/or augment HBV expression levels.

SUMMARY OF THE INVENTION

The present invention relates to novel methods and compositions for establishing hepatitis B virus (HBV) gene expression and replication using recombinant HBV baculovirus to deliver the HBV genome to cells in culture.

The invention relates a method for selecting a candidate agent to reduce hepatitis virus expression in human cells, said method comprising:
(a) infecting the cells with a genetic construct comprising at least a part of a baculovirus genome and a greater than a full length hepatitis virus genome, such that it is replication competent, a novel approach;
(b) contacting the infected cells with the candidate agent,
(c) determining whether there is less expression of the hepatitis virus in the contacted cells than in an infected cell that is not contacted with the candidate agent; and
(d) selecting the candidate agent if there is less expression. A suitable candidate agent is 3TC lamivudine. Suitable cell lines are HepG2 or Huh-7. A suitable candidate agent is an antiviral agent or cytokine.

An aspect of the present invention is a hepatic cell infected with a genetic construct comprising at least a part of a baculovirus genome and more than a full length HBV genome such that it is replication competent.

A suitable HBV virus genome that is in the genetic construct is a 1.3-genome length HBV construct which is capable of driving high levels of HBV replication.

An aspect of the invention is a method for determining parameters of HBV infection, said method comprising synchronously initiating HBV replication efficiently in a high, i.e.; about 50–100% percentage of cells of hepatic origin without toxicity to the cells.

An aspect of the invention is a method for transient delivery of high level mammalian gene expression to a cell of hepatic origin using endogenous HBV enhancer and promoter sequences.

Cell lines suitable for practice of the present invention include human cell lines of hepatic origin, e.g. HepG2 and Huh-7. An aspect of the invention is that HBV gene expression is driven exclusively from endogenous promoters, a condition that mimics a natural infection. The methods and compositions of the present invention are alternatives to stable HBV-expressing cell line models and cell lines transiently transfected at low efficiencies by classical procedures. In HBV baculovirus infected cells, HBV transcripts and intracellular and secreted HBV antigens are produced; replication occurs, as evidenced by the presence of high levels of intracellular replicative intermediates and protected HBV DNA in the medium. Density-gradient analysis of extracellular HBV DNA indicated that the DNA was contained predominantly in enveloped HBV virions. Covalently closed circular (CCC) DNA is also present indicating that, in this system, HBV core particles are capable of delivering newly synthesized HBV genomes back into the nuclei of infected cells.

An aspect of the invention is that the effects of specific agents (antivirals) cytokines, and so forth) on hepatitis virus gene expression and replication may be tested. This results in a system that can be used to evaluate the efficacy of antivirals for HBV. An HBV recombinant virus system can be used to analyze the effect of an antiviral on HBV replication and on CCC DNA formation. Use of recombinant HBV baculovirus to study HBV replication in cell culture is not limited to the HepG2 cell line but can be extended to the Huh-7 hepatoma cell line and primary human hepatocytes.

Levels of HBV gene expression and replication were achieved in HBV baculovirus-infected HepG2 cells which far exceed levels found in HepG2 2.2.15 cells using previously available methods. In the present invention, HBV baculovirus infection of HepG2 cells lends itself readily to manipulation as follows: 1) HBV expression can be initiated any time relative to seeding of HepG2 cells; 2) levels of HBV replication can be regulated over a wide range simply by changing the baculovirus multiplicity of infection; 3) HBV replication is readily detectable by one day post infection with HBV baculovirus and is detectable at least through day eleven post infection; and (4) the transient nature of the infection can be extended and/or enhanced by superinfecting the cultures. Infection of HepG2 cells by HBV recombinant baculovirus represents a simple to use and highly flexible method for assaying the effects of antivirals and/or cytokines on HBV production, and for understanding HBV replication and pathogenesis at the molecular level.

Abbreviations used herein: HBV: hepatitis B virus; CCC: covalently closed circular; moi: multiplicity of infection; HBsAg: hepatitis B surface antigen; HBeAg: hepatitis B e antigen; LDH: lactate dehydrogenase; HbcAg: hepatitis B core antigen; pfu: plaque forming units.

BRIEF DESCRIPTION OF THE DRAWINGS

The file of this patent contains at least one drawing excuted in color. Copies of this patent with color drawings will be provided by the Patent and Trademark Office upon request and payment of the necessary fee.

FIG. 4 presents an analysis of HBV transcripts in HepG2 cells infected with HBV baculovirus.

FIG. 18 shows the treatment schedules used for analyzing the effect of 3TC on vaculovirus infected HepG2 cells.

DETAILED DESCRIPTION OF THE INVENTION

Figure 1:
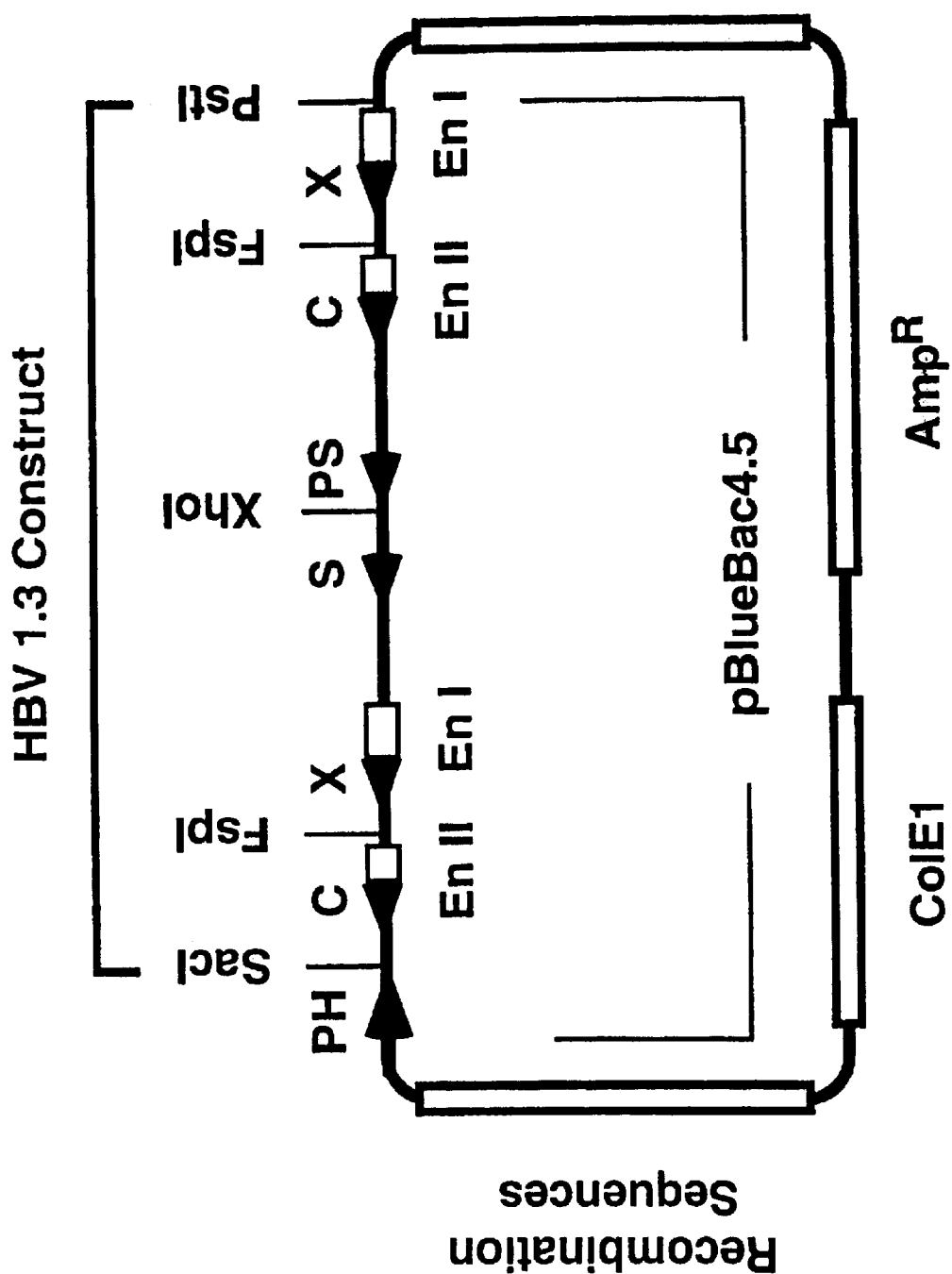
FIG. 1 shows a map of an HBV transfer vector pBB45HBVI.3. The HBV core (C), X, pre-S (PS), and S promoters (S), as well as enhancer I (En I) and enhancer II (En II) sequences are indicated. Arrows ([pic of arrow]) indicate promoter location and the direction of transcription; ( ) enclose enhancer sequences.

The invention relates generation of a baculovinus containing the HBV 1.3 construct; combining the recombinant HBV 1.3 baculovirus with HepG2 cells to generate the novel in vitro cell culture system for replicating HBV described; and demonstrates that baculovirus can transfer genetic information under the control of HBV promoters and enhancers into HepG2 cells.

The HBV baculovirus infected cell system of the present invention represents a new method for using cells to study HBV. Suitable cells include HepG2 and Huh-7. Indeed, the HBV baculovirus system, like 2.2.15 cells, can be used to evaluate the effect of nucleosides, cytokines, and/or novel drugs on HBV replication. Similarly, the HBV baculovirus system, like HepG2 transiently transfected by more classical means, can be used for understanding HBV replication and pathogenesis and the function of specific HBV gene products and regulatory elements at the biological, genetic, or molecular level. The HBV baculovirus infected cell system, because of its simplicity and flexibility, is useful extensively in studies on HBV and to develop agents to prevent infection or reduce HBV's clinical effects.

This invention which relates novel transient compositions and methods for studying HBV in cell lines such as the well differentiated human hepatoblastoma cell line HepG2, and Huh-7 has certain advantages as follows:

1) Recombinant HBV baculovirus is an efficient vector for the delivery of HBV genetic information to human cells and can be used to initiate HBV gene expression and replication in the cells. HBV transcripts, intracellular and secreted HBV antigens, are produced and replication occurs as evidenced by the presence of high levels of intracellular replicative intermediates and protected HBV DNA in the medium. CCC DNA is present indicating that, in this system, HBV core particles are capable of delivering newly synthesized HBV genomes back into the nucleus of infected cells. Strong HBV gene expression can be detected as early as one day post-infected (p.i). High levels of HBV replicative intermediates, extracellular DNA, and CCC DNA persist through at least eleven days p.i.

2) Endogenous HBV enhancers and promoters are used to obtain high evels of HBV expression and replication in the cells.

3) The level of HBV expression and replication in the cells infected with HBV baculovirus can be altered over a considerable range simply by changing the moi. Levels of HBV gene expression and replication can be achieved in HBV baculovirus infected HepG2 cells that far exceed the levels found in 2.2.15 cells.

4) HBV baculovirus mediated HBV replication is a transient system and does not require integration of the HBV viral genome.

5) HBV baculovirus infection, even at high multiplicities, is not toxic to cells HepG2 or Huh-7.

6) HBV expression can be enhanced or prolonged in a population of HBV baculovirus infected cells simply by superinfection of the cultures.

One major difference between baculovirus-mediated gene transfer of HBV to HepG2 cells and stably transfected cell lines is the ability to synchronously initiate the replication process. In a stably transfected HBV cell line, such as 2.2.15, each cell contains virus at all phases of the replication cycle. In contrast, HBV baculovirus infection can be used to synchronously start HBV replication in e.g., HepG2 cells because these cells contain no viral products before infection. In HBV baculovirus infected HepG2 cells, it was possible to follow the time course for secretion of both HBsAg and HBeAg with time after infection. The rise in HBsAg temporally preceded the detection of secreted HBeAg. HBV antigens were detectable in the media of infected cells at the first time point tested, one day after exposure to the HBV baculovirus. Maximal levels of protein secretion were generally observed on day three p.i. for HBsAg and day five p.i. for HBeAg. When HepG2 cells infected with HBV baculovirus at day one were reinfected at day four, the HBsAg levels rose immediately, whereas the rise in HBeAg was delayed in the same fashion as had been observed when infection was at day one.

Use of baculovirus for gene transfer and expression in mammalian cells is enhanced. It has been previously reported that baculovirus containing genes driven by strong viral promoters such as Rous sarcoma virus and cytomegalovirus can be used to achieve gene expression in cells of hepatic origin. Recombinant baculovirus encoding genes which are driven by the promoters and enhancers present in HBV can be used quite effectively in the absence of exogenous promoters to drive high levels of gene expression in HepG2 cells.

HBV replication in HBV baculovirus infected HepG2 cells has some distinct similarities to HBV replication in humans. HBsAg is detected in the medium before HBeAg which is similar to that observed in an acute HBV infection in that HBsAg is found in the serum before HBeAg. With regard to HBV transcript production, no aberrant transcripts are present and the level of the pregenomic 3.5-kb transcript is high. The one aspect of the replication cycle that is lacking in the HBV baculovirus system is receptor-mediated infection. However, to date there is no stable or transient in vitro system which can be used to study HBV infection via its natural receptor. It is possible to simulate reinfection that would occur in a natural host using the HBV baculovirus system by superinfecting HepG2 cells in culture.

The 2.2.15 cell line, which has been used extensively as an in vitro test system for evaluating the efficacy of antivirals, was generated by stable transfection of HepG2 cells with the pDoITHBV-1 plasmid, which contains two head-to-head dimers of the HBV genome between Moloney Murine leukemia virus long terminal repeats. Thus, in 2.2.15 cells, HBV gene expression is driven by heterologous promoters as well as internal endogenous HBV promoters. It is clear from previous studies using transient transfection of HepG2 cells with HBV genetic information and generation of stable transfected cell lines that HepG2 cells express the appropriate transcription factors to interact with the endogenous HBV promoters and enhancers and can drive HBV expression in the absence of strong foreign promoters. However, the levels of HBV expression have been modest. HepG2 cells indeed have the capacity to drive extremely high levels of HBV expression utilizing only endogenous HBV promoters and enhancers. HBV antigen production did approach saturation when an moi of 100 to 200 pfu/cell was reached.

There are several other distinct differences between the HBV baculovirus infected HepG2 cell system and 2.2.15 cells. The 2.2.15 cell contains approximately eight integrated HBV genomes; the level of HBV expression is, therefore, limited by this copy number. This is not the case for HBV baculovirus infected HepG2 cells. A striking feature of baculovirus-mediated gene transfer is that HBV expression is dose dependent and can be altered over an extensive range simply by changing the moi. Below an moi of 100 pfu, HBV baculovirus/per cell levels of secreted HBsAg and HBeAg produced by HepG2 cells are directly proportional to the viral dose administered. In addition to secreted antigens, all other viral products tested, including HBV transcripts, replicative intermediates, and CCC DNA, were also present at levels proportional to the moi. Because the baculovirus system can be regulated simply by changing the moi, it is possible to evaluate not only whether an antiviral and/or cytokine can reduce an existing level of HBV virion production, but also to determine the range of efficacy of a drug to clear a low level of infection or reduce or eliminate greater amounts of the virus. This flexibility with regard to the level of HBV expression and replication will also be of value in molecular studies aimed at understanding the viral replication cycle and viral pathogenesis.

Another factor which must be taken into consideration with regard to the level of HBV expression in HBV baculovirus infected HepG2 cells is the content of HBV sequences that are present within the baculovirus. Specifically, the HBV baculovirus was generated using a 1.3-genome length HBV construct, which contains two HBX open reading frames and enhancer promoter regions. It has been previously demonstrated that a 1.2-genome length HBV construct, containing only one HBX open reading frame, is sufficient for generating transgenic mice that express HBV and an HBV-producing cell line. It is possible that the presence of two HBX open reading frames and/or regulatory sequences may have a stimulatory effect on HBV expression by HBV baculovirus.

One additional difference between the HBV baculovirus system and 2.2.15 cells is the number of days the cells need to remain in culture before they can be used for an experiment. Because HBV expression in 2.2.15 cells is low, it is often necessary to grow 2.2.15 for a week or more and to high densities to detect HBV DNA in the medium. In contrast, extracellular HBV virions can be readily detected in the medium of HepG2 cells as early as two days p.i. with HBV baculovirus.

HBV baculovirus mediated infection of HepG2 cells also has the advantage of being highly flexible for experimental manipulation. For example, HBV expression can be initiated at any time relative to seeding of HepG2 cells. Therefore, the cells can be pretreated with antivirals, hormones, growth factors, cytokines, etc., before or after HBV baculovirus infection. Similarly, the density of HepG2 cells at the time of initiation of HBV gene expression can be predetermined. For these reasons, it is possible to manipulate the physiology of HepG2 cells independent of viral gene expression and replication.

There are several advantages of using baculovirus infection as a transient delivery system instead of electroporation or more classical calcium phosphate or polycationic lipid based transfection methods. Foremost may be the extremely high percentage of transfected cells that baculovirus mediated gene delivery affords. Between 75% to 85% of HepG2 cells in a infected population stain positive for HBcAg. This efficiency is significantly higher than what has been reported for standard calcium phosphate, lipid-mediated, and other viral vectors which have typically resulted in transfection efficiencies in HepG2 cells of at best 20%. In addition, baculovirus mediated gene transfer is not toxic, even at high multiplicities, and does not require extensive manipulation or incubation of HepG2 cells.

Another important characteristic of the HBV baculovirus system is that at any time p.i., the cells can be superinfected with additional doses of recombinant baculovirus. Superinfection has several advantages. First, it makes it possible to increase the level of HBV gene expression at any predetermined time point with minimal manipulation of the cells. Second, it makes it possible to complement or alter HBV expression by introducing a second or even a third gene. For example, superinfection could be carried out with baculoviruses carrying mutated forms of HBV or entirely different genes. Indeed, either through confections or superinfection, this system can be easily used to examine complementation by two or more mutated HBV genomes.

Use of the HBV baculovirus to study HBV replication is not limited to one cell type, HepG2 cells. Other cell types, e.g. Huh 7 cells, are also suitable.

EXAMPLES

The following examples are presented to illustrate aspects of the invention.

EXAMPLE 1

Generation of an HBV Baculovirus

The invention includes generation and use of a recombinant baculovirus which includes at least a part of an HBV genome and therefore is capable of initiating HBV replication in the HepG2 cell line. Transcription of linear HBV DNA requires a greater than unit length 3.2-kb HBV genome to produce the 3.5-kb pregenomic message which is required for replication. This has been accomplished by others by developing multimeric or terminally redundant HBV DNA constructs. The recombinant baculovirus of the present invention encodes a 1.3-genome length HBV construct. This construct contains two complete HBV X protein (HBX) open reading frames as well as two enhancer I/X promoter regions and was used because this construct was previously shown to drive high levels of HBV replication in the livers of transgenic mice. (Guidotti et al., 1995) The nature and magnitude of HBV expression and replication obtainable in HepG2 cells infected with the recombinant HBV encoding baculovirus was determined. For comparative purposes, the 2.2.15 cell line was used.

FIG. 1 shows a map of an HBV transfer vector: pBB45HBV1.3. A Pstl/Sacl fragment containing the entire 1.3-genome length HBV construct was excised from pTHBV1.318 and cloned into the baculovirus transfer vector pBlueBac4.5 (Invitrogen). The 1.3-HBV construct is in an antisense orientation with respect to the baculovirus polyhedrin promoter (PH). The HBV core (C), X, pre-S (PS), and S promoters (S), as well as enhancer I (En I) and enhancer II (En II) sequences are indicated. The four HBV promoter and two enhancer sequences are endogenous to the HBV genome and function to drive transcription of the HBV genes. Arrows ([pic of arrow]) indicate promoter location and the direction of transcription; ( ) enclose enhancer sequences.

Figure 2:
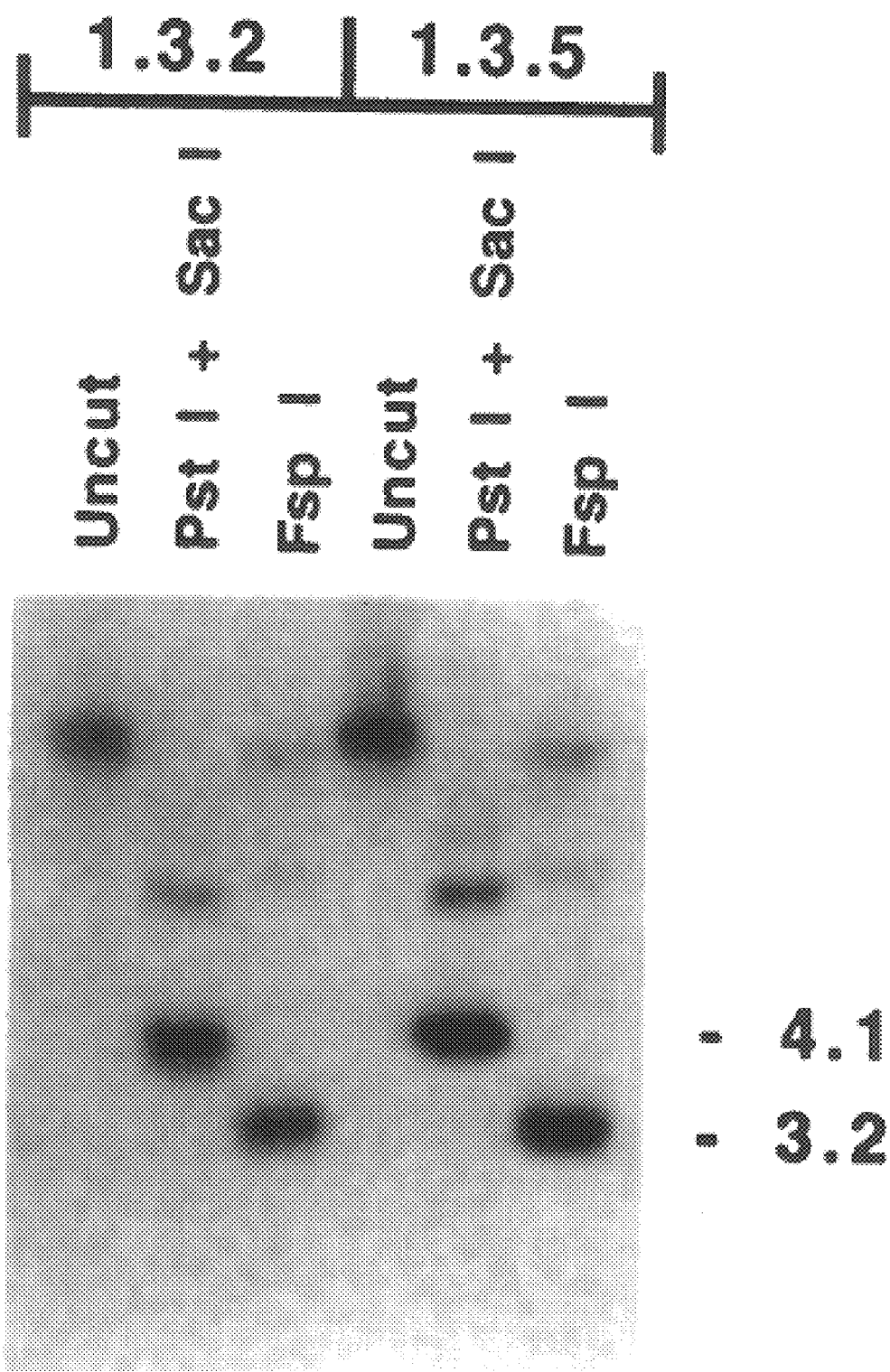
FIG. 2 illustrates a stable integration of the full length 1.3-HBV construct into recombinant baculoviruses.

FIG. 2 illustrates the stable integration of the full length 1.3-HBV construct into recombinant baculoviruses. Southern blot analysis was performed on DNA extracted from amplified recombinant HBV baculoviruses. Genomic baculovirus DNA was uncut, digested with Pstl/Sacl to release the 4.1-kb full length 1.3-HBV construct, or digested with Fspl to release a 3.2-kb unit length HBV monomer. An additional unexpected higher molecular weight band was observed after Pstl/Sacl digestion, and most likely represents a partial digestion product. Two recombinant isolates, 1.3.2 and 1.3.5, which contained the full length HBV 1.3 construct were analyzed. Plasmid DNA containing the 1.3 construct was digested with the same enzymes and used as molecular size markers.

A 1.3genome length HBV construct was provided by Dr. Heinz Schaller (University of Heidelberg, Heidelberg, Germany). This construct previously was shown to drive high levels of HBV replication in the livers of transgenic mice. (Guidotti et aL, 1995) The 1.3-HBV construct was excised from pTHBV1.3 and cloned into the baculovirus transfer vector pBlueBac4.5. The recombinant transfer vector, pBB45HBV1.3 (FIG. 1), was cotransfected into Sf21 cells together with linear baculovirus DNA. Approximately 70% of the recombinant viruses isolated by plaque assay had integrated the 1.3-HBV construct, as determined by Southern blot analysis. Two isolates containing the full length construct, designated 1.3.2 and 1.3.5, were further amplified, concentrated, and purified. Purified virus was re-examined by Southern blot which demonstrated that the entire HBV construct remained stably integrated within the baculovirus genome (FIG. 2). The same result was obtained for both the 1.3.2 and 1.3.5 viruses. The 1.3.5 virus was used for all subsequent procedures disclosed herein. Purified viral stocks were titered in Sf21 cells and titers of $5 \times 10^9$ pfu/mL were routinely obtained.

EXAMPLE 2

Secretion of HBV Antigens by Infected HepG2 Cells

The ability of HBV baculovirus 1.3.5 to express HBV gene products after infection of HepG2 cells was tested by monitoring conditioned medium for the presence of HBsAg and HBeAg. HepG2 cells were infected at multiplicities ranging from 3.1 to 400 pfu/cell and conditioned medium was collected daily from each sample for analysis of HBsAg and HBeAg by radioimmunoassay. The 2.2.15 cell line was used as a positive control. 2.2.15 cells were seeded at the same density as HepG2 cells and all cells reached confluence approximately one week into the experiment.

FIG. 3 presents an analysis of HBV antigens in the medium of HepG2 cells infected with HBV baculovirus (A and B) with respect to moi (multiplicity of infection) with HBV baculovirus and (C and D) with respect to time p.i. (post infection). HepG2 cells were seeded in 35-mm dishes and infected the following day at multiplicities of 0, 3.1, 6.25, 12.5, 25, 50, 100, 200, and 400 pfu/cell. 2.2.15 cells were seeded at the same density and used as a positive control.

Media exposed to the cells for 24 hours were collected from each set of cells at three days p.i. and analyzed for the presence of (A) HBsAg and (B) HBeAg by radioimmunoassay. HBsAg and HBeAgs are gene products encoded by the HBV surface and core open reading frames respectively. HBsAg and HBeAg are secreted by HBV producing cells. HBsAg and HBeAg levels in the serum of patients are measured and used to evaluate the course of the HBV infection. HBsAg and HBeAg levels detected in the medium of 2.2.15 cells are indicated on each panel by an arrow. HepG2 and 2.2.15 cells were seeded as described for (A and B) and HepG2 cells were infected with HBV baculovirus at an moi of 0, 6.25, 25,100, and 400 pfu/cell. Conditioned medium was collected daily from each set of cells for fifteen days and analyzed for the presence of (C) HBsAg and (D) HBeAg by radioimmunoassay. (C and D, ) On day four p.i., a culture of HepG2 cells originally infected at an moi of 100 was superinfected with an additional 100 pfu/cell.

Figure 3A:
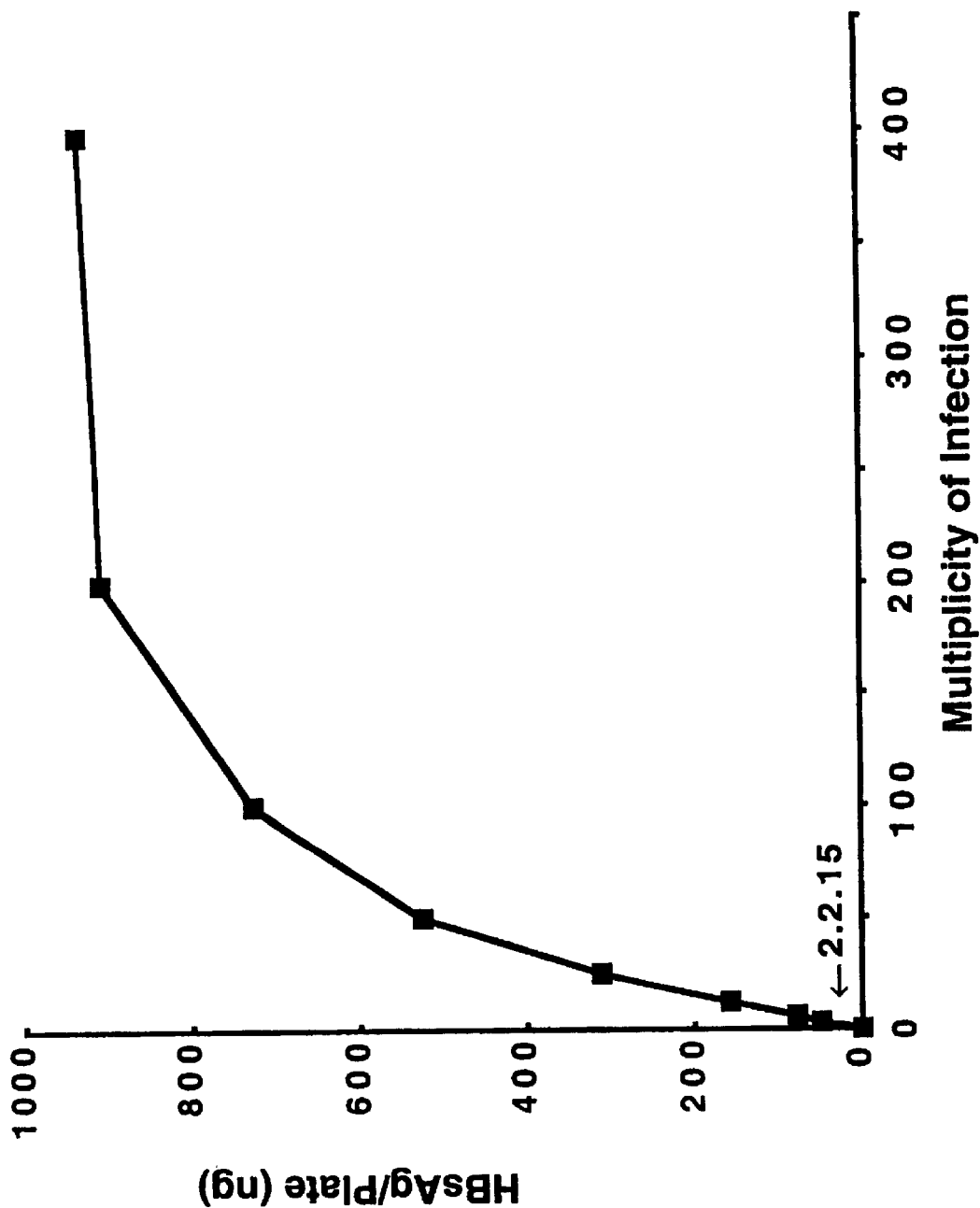
FIG. 3 presents an analysis of HBV antigens in the medium of HepG2 cells infected with HBV baculovirus (A and B) with respect to moi (multiplicity of infection) with HBV baculovirus and (C and D) with respect to time p.i. (post infection). HBsAg and HBeAg levels detected in the medium of 2.2.15 cells are indicated on each panel by an arrow.
Figure 3B:
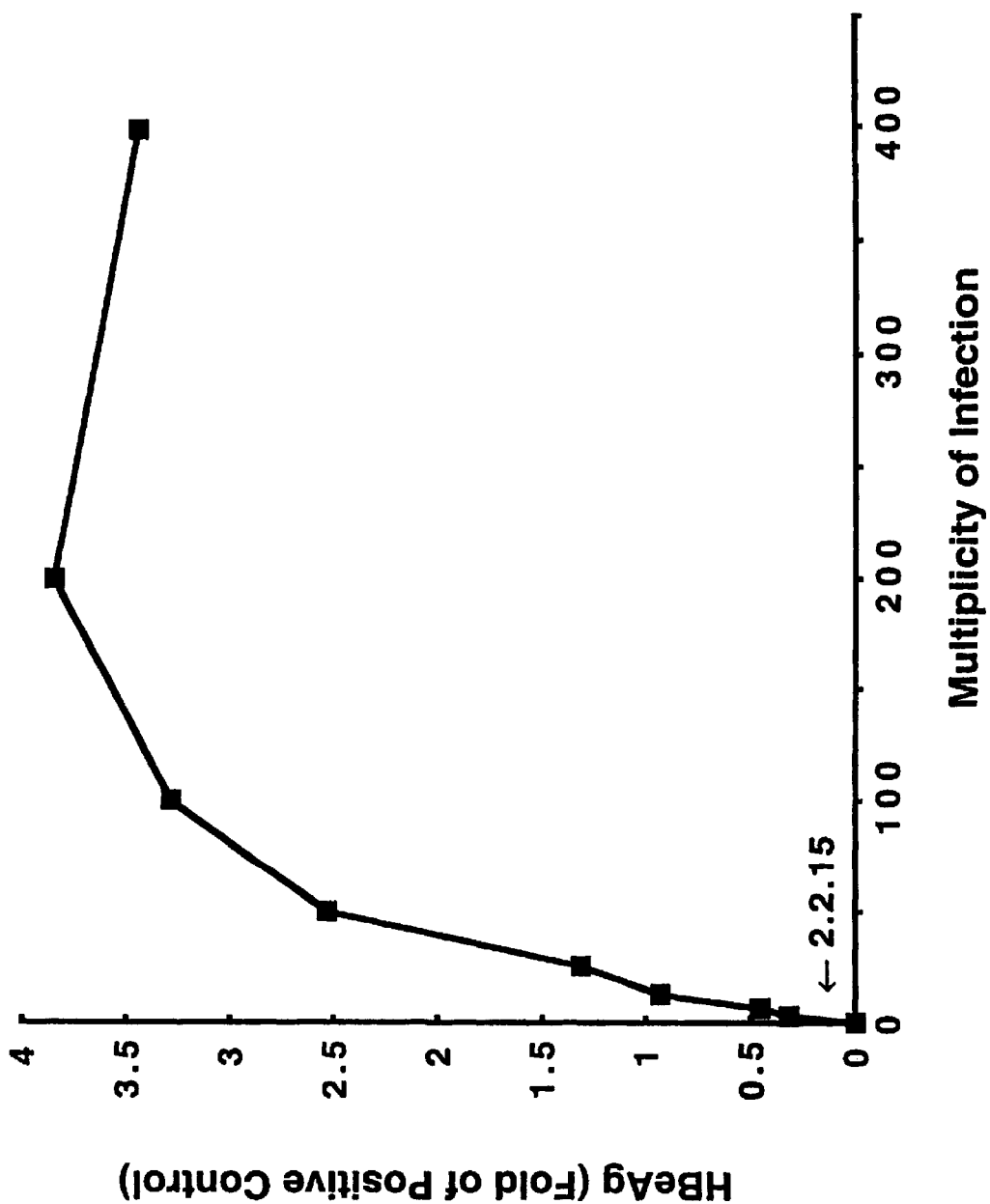

FIGS. 3A and 3B demonstrate the dose dependent production of HBsAg and HBeAg by HepG2 cells infected with HBV baculovirus. At an moi of less than 100 pfu/cell, the amount of HBsAg and HBeAg in the medium was directly proportional to the moi. The production of both HBV antigens became saturated between an moi of 100 and 200 pfu/cell. HBsAg produced by HBV baculovirus infected HepG2 cells ranged from approximately 2- to 35-fold the level produced by the 2.2.15 cell line. HBeAg production by infected HepG2 cells was 1.4 to 17 times higher than that of 2.2.15.

Figure 3C:
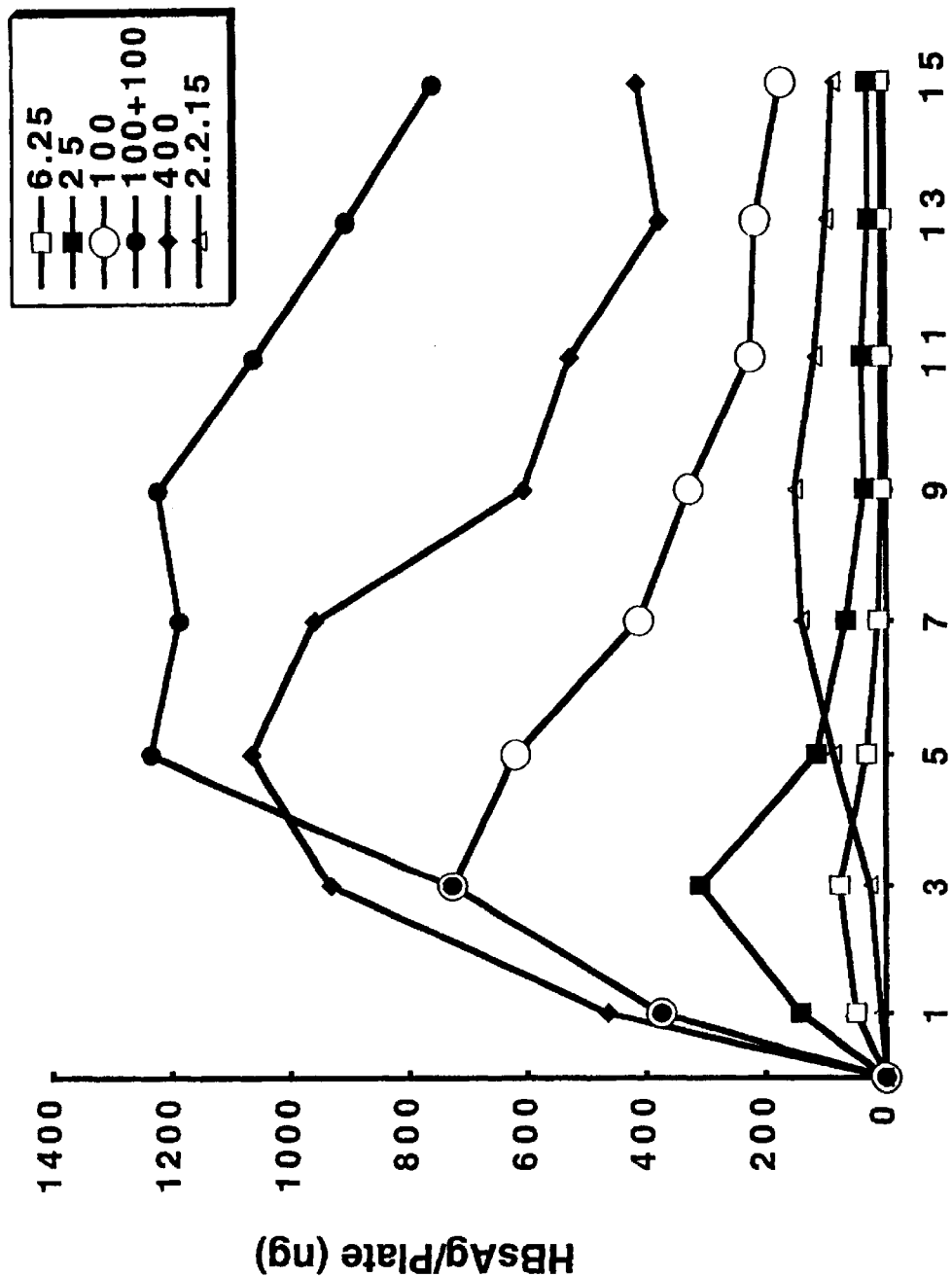
Figure 3D:
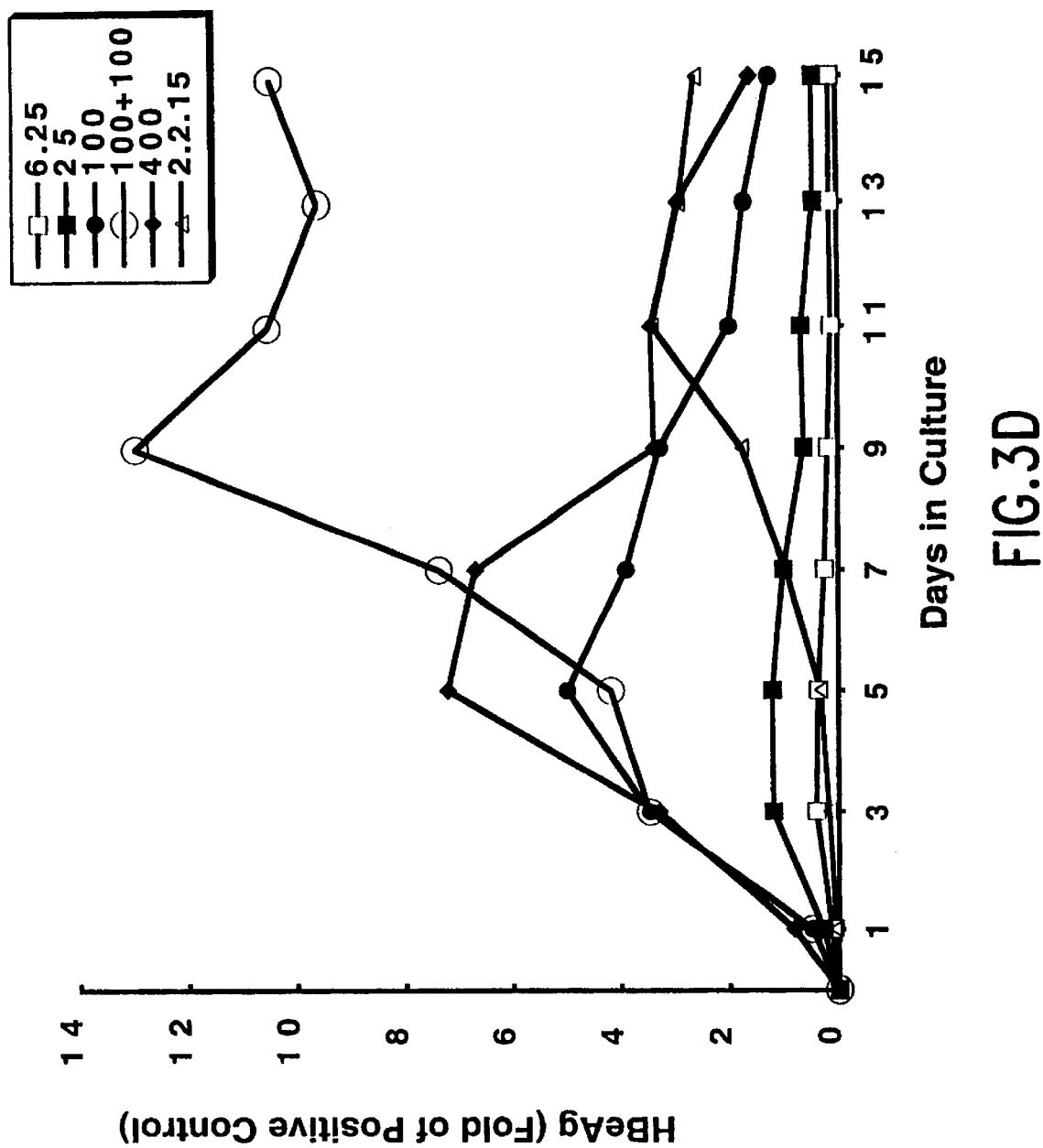

The expression of secreted HBV antigens were examined over a two-week period (FIGS. 3C and 3D). HBsAg levels reached maximal levels approximately three days p.i. Maximal levels of HBeAg were generally produced five days p.i., slightly later than for HBsAg. After reaching a maximal level, each antigen exhibited a steady decline during the remainder of the two-week time course. This was expected, because the baculovirus genome does not integrate and should randomly segregate and/or be lost during cell division. Levels of both antigens remained detectable in the medium of cells infected at all multiplicities. The time course for HBV antigen expression in HBV baculovirus infected HepG2 cells was considerably different than was found in the 2.2.15 cell line. The level of HBV antigens in medium from 2.2.15 cells exhibited a steady increase through day nine (HBsAg) and eleven (HBeAg) after seeding, consistent with what has previously been reported for the 2.2.15 cell line.

To determine whether HBV baculovirus infection had a toxic effect on HepG2 cells, medium samples from cells infected at an moi of 100 pfu/cell were assayed for the presence of the cytoplasmic enzyme LDH. Medium samples collected at 24-hour intervals were assayed for LDH activity and compared with the total LDH activity present in the cultures following the release of intracellular LDH. Triplicate cultures of infected and mock infected cells were analyzed at one, two, three, four, five, and seven days p.i. (Table 1). Similar levels of LDH were detectable in the medium of infected and mock infected cells at one day p.i. Less than 1.0% of the total LDH activity was found in the medium of infected or mock infected cultures on days two to seven p.i. The presence of extracellular LDH in mock infected cultures on day one p.i. suggests that the observed toxicity is not caused directly by the baculovirus, but rather by the exposure of the cells to a low volume of medium during the one-hour incubation period and the subsequent washing procedure. These findings indicate that baculovirus infection is not toxic to HepG2 cells, and that detection of HBeAg in the medium does not simply represent the release of intracellular HBc/eAg.

TABLE 1

Detection of LDH Released Into the Medium of HBV Baculovirus Infected and Mock-Infected HepG2 Cells

| | % Extracellular LDH Activity | |
| --- | --- | --- |
| Days p.i. | Infected (mol 100) | Mock Infected |
| 1 | 5.90 ± 0.75 | 8.07 ± 3.47 |
| 2 | <0.5 | <0.5 |
| 3 | 0.65 ± 0.40 | <0.5 |
| 4 | <0.5 | 0.86 ± 0.73 |
| 5 | <0.5 | <0.5 |
| 7 | <0.5 | <0.5 |

NOTE. Extracellular LDH activity is expressed as the percentage of LDH activity present in medium after exposure to HepG2 cultures for 24 hours relative to the total amount of LDH activity present in the cultures following release of intracellular LDH at the end of the 24-hour time point. Each group was analyzed in triplicate and the standard error (SE) for each group is indicated.

EXAMPLE 3

Superinfection of Infected HepG2 Cells with HBV Baculovirus

To determine whether levels of HBV expression could be further elevated in HepG2 previously infected with HBV baculovirus, the effect of superinfection in this system was analyzed. Specifically, four days after an initlal infection with 100 pfu of 1.3.5 virus/cell, HepG2 cells were superinfected with an additional 100 pfu/cell. Medium samples were collected daily from superinfected cells and analyzed for HBV antigens by radioimmunoassay. HBsAg and HBeAg levels increased dramatically following the second infection (FIGS. 3C and 3D).

EXAMPLE 4

Expression of HBV Transcripts

The size and abundance of HBV transcripts produced by HBV baculovirus infected HepG2 cells were examined. Because the production of HBsAg and HBeAg became saturated when infecting at multiplicities above 100 pfu/cell, these and subsequent studies were carried out using viral doses of 100 pfu/cell or less. Total RNA was isolated from HepG2 cells four days p.i. and analyzed by Northern blotting. The 3.5-, 2.4-, and 2.1-kb transcripts were detectable in HepG2 cells infected with 1.3.5 virus at multiplicities ranging from 5 to 100 pfu/cell (FIG. 4A).

FIG. 4 presents an analysis of HBV transcripts in HepG2 cells infected with HBV baculovirus. HepG2 cells were seeded in 100-mm plates and infected the following day at multiplicities of 0, 5, 25, 50, and 100 pfu/cell. 2.2.15 cells were seeded at an equal density and used as a control. Four days p.i., total RNA was extracted from all cells. (A) Twenty micrograms of total RNA was r5- analyzed by Northern blotting. The 3.5-, 2.4-, and 2.1-kb transcripts are indicated. (B) On a longer exposure of the blot, the 2.4- and 2.1-kb transcripts were detectable in RNA samples from 2.2.15 cells. (C) A photograph of the ethidium bromide stained RNA gel indicates equal loading of RNA samples.

Overexposure of Northern blots from HepG2 cells infected with 1.3.5 virus at multiplicities of 25 to 100 pfu/cell also resulted in a faint band at approximately 0.7 kb. Transcript levels among HBV baculovirus infected HepG2 cells were proportional to the moi. The 3.5-kb message was the most strongly expressed messenger RNA. At an moi of 25, the level of expression of the 3.5-kb HBV RNA was considerably higher than in 2.2.15 cells. The ratio of expression of the three transcripts relative to each other is similar in infected HepG2 cells compared to 2.2.15 cells (FIG. 4B).

EXAMPLE 5

Detection of HBV Replicative Intermediates In Cytoplasmic Core Particles

To evaluate HBV genome replication, cytoplasmic cores were prepared from HepG2 cells infected with HBV baculovirus at four days p.i. with multiplicities ranging from 5 to 100 pfu HBV baculovirus/cell.

FIG. 5 presents an analysis of HBV replicative intermediates from intracellular core particles in HepG2 cells infected with HBV baculovirus. HepG2 cells were seeded in 100-mm dishes and infected the following day with 0, 5, 25, 50, and 100 pfu/cell. 2.2.15 cells were seeded at an equal density as a control. Four days p.i. core particles were prepared from the cytoplasm of all cells. (A) DNA extracted from core particles was analyzed by Southern blotting. Bands corresponding to relaxed circular DNA (RC) double stranded linear DNA (DS) and single stranded DNA (SS) are indicated. One-hundred programs of linear HBV DNA and HindIII cut lambda DNA (data not shown) were used as molecular size markers. (B) A longer exposure of the blot is provided to visualize replicative intermediates produced by 2.2.15 cells.

Figure 5A:
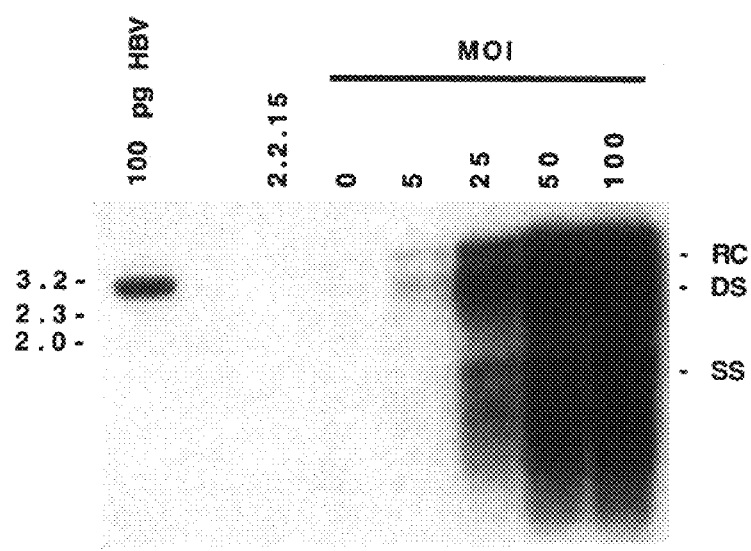
FIG. 5 presents an analysis of HBV replicative intermediates from intracellular core particles in HepG2 cells infected with HBV baculovirus.

Nucleic acid was extracted from cytoplasmic core particles and subjected to Southern blot analysis (FIG. 5A).

Figure 5B:
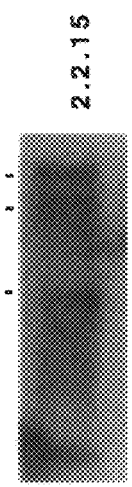

HBV replicative intermediates were detectable in HepG2 cells at levels proportional to the moi and at an moi as low as 5 pfu/cell. Prominent bands corresponding to relaxed circular (RC), double stranded linear (DS), and single stranded (SS) DNAs were present as well as a smear of molecules of intermediate and lower molecular weight. The ratio of RC, DS, and SS molecules were approximately the same in HBV baculovirus infected HepG2 cells as in 2.2.15 cells, but levels of replicative intermediates were higher in HBV baculovirus infected HepG2 cells (FIG. 5B).

EXAMPLE 6

Detection of CCC DNA

Figure 6:
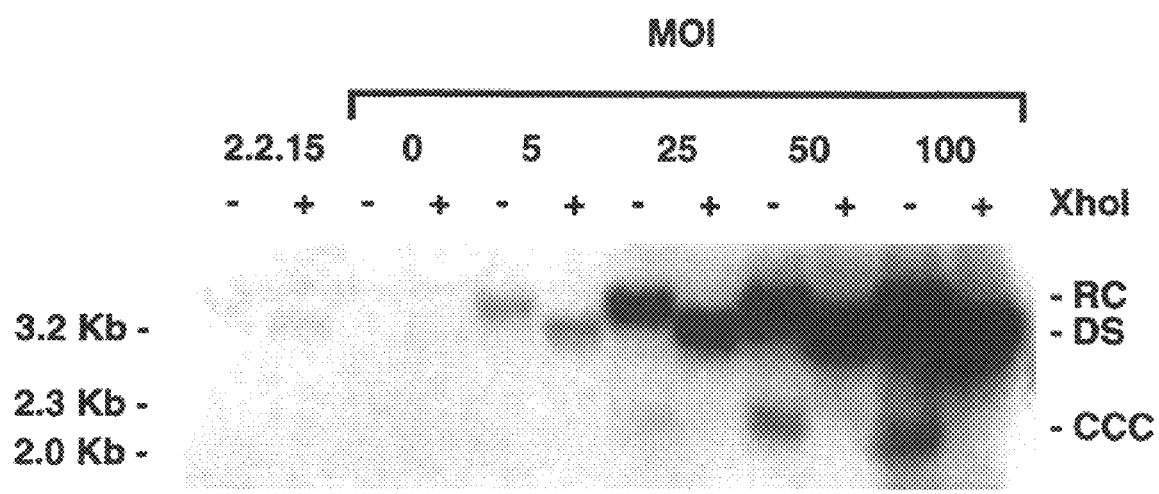
FIG. 6 presents an analysis of CCC DNA in HepG2 cells infected with HBV baculovirus.

CCC HBV DNA levels were measured in infected HepG2 cells. FIG. 6 presents an analysis of CCC DNA in HepG2 cells infected with HBV baculovirus. HepG2 cells were seeded in 100-mm dishes and infected the following day with 0, 5, 25, 50, and 100 pfu/cell. 2.2.15 was seeded at an equal density and used as a positive control. Seven days p.i., low molecular weight DNA was extracted from all cells. Low molecular weight DNA was digested with RNase and an exonuclease which degrades linear, but not circular DNA. Before Southern analysis, one half of each sample was digested with XhoI to convert circular HBV genomes into linear DNA. Bands corresponding to relaxed circular (RC), double stranded linear DNA (DS), and supercoiled circular DNA (CCC) are indicated. Linear HBV DNA and HindIII cut lambda DNA were used as molecular size markers.

Nonprotein-bound low molecular weight DNA was extracted from HepG2 cells seven days p.i. Low molecular weight DNA was digested with Plasmid-Safe ATP-Dependent DNase, (an exonuclease which degrades both single and double stranded linear DNA), and was then subjected to electrophoresis and Southern blotting. Relaxed circular and CCC DNA are resistant to digestion by this exonuclease. Infected HepG2 cells at all multiplicities tested contained circular HBV genomes (FIG. 6). Two species of circular DNA were present, a relaxed circular molecule (RC) and a faster migrating supercoiled molecule (CCC). The RC form was present at higher concentrations. Both circular DNAs were converted into a 3.2-kb double stranded linear DNA (DS) after restriction with XhoI, an enzyme which cleaves the HBV genome once. The copy number of circular genomes present increased proportionally with moi. HepG2 cells infected with HBV baculovirus at an moi as low as 5 pfu/cell contained higher levels of CCC HBV DNA than 2.2.15 cells.

EXAMPLE 7

Detection of Extracellular HBV DNA

Figure 7:
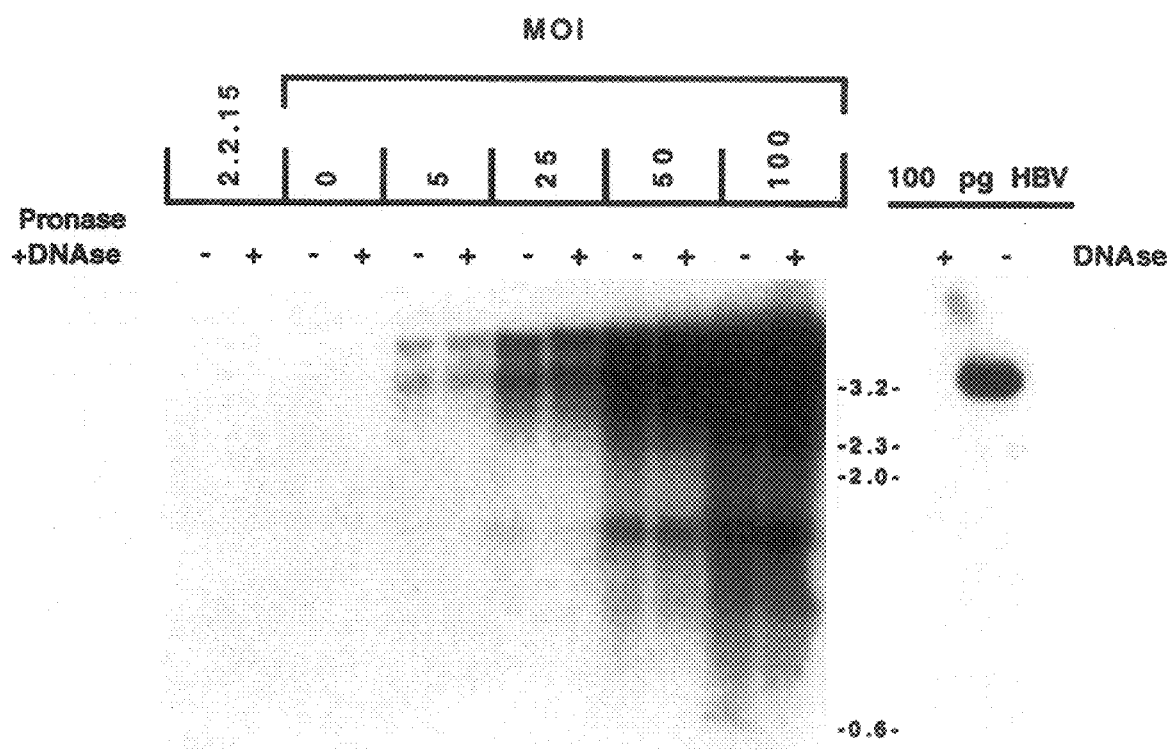
FIG. 7 presents an analysis of extracellular HBV DNA produced by HepG2 cells infected with HBV baculovirus.

To assess whether infected HepG2 cells were producing viral particles, medium from infected HepG2 cells was assayed for the presence of protected HBV DNA. FIG. 7 presents an analysis of extracellular HBV DNA produced by HepG2 cells infected with HBV baculovirus. HepG2 cells were seeded in 100-mm dishes and infected the following day with 0, 5, 25, 50, and 100 pfu/cell. 2.2.15 was seeded at an equal density. All cells were fed 10 mL of medium per dish on day two p.i. and conditioned medium was collected 48 hours later on day four p.i. HBV particles were precipitated and collected from each medium sample. One half of each sample was digested sequentially with Pronase and DNase to digest unenveloped, unencapsidated DNA. DNA was then extracted from all samples and analyzed by Southern blotting. One-hundred programs of linear HBV DNA and HindIII cut lambda DNA were used as molecular size markers.

Medium exposed to the cells for 48 hours (day two to day four p.i.) was harvested. Virions were concentrated from the medium and assayed for HBV DNA content. The production of extracellular HBV DNA by infected HepG2 cells was proportional to the moi (FIG. 7). Sequential treatment of the samples with Pronase and DNase had no significant effect on DNA levels indicating that nearly all of the extracellular DNA present was contained in encaspidated, enveloped particles. DNA extracted from these extracellular particles had a higher proportion of RC and DS molecules than SS molecules compared to the HBV DNA extracted from the cytoplasm suggesting that a majority of particles outside the cell had completed second DNA strand synthesis. Four days after seeding, extracellular HBV DNA from 2.2.15 cells was not detected. However, extracellular HBV DNA was detected previously in medium from 2.2.15 cells in culture for greater than seven days post seeding.

EXAMPLE 8

Gradient Analysis of Extracellular HBV Particles Produced by HBV Baculovirus Infected Cells To further investigate the nature of extracellular HBV DNA secreted by HBV baculovirus infected HepG2 cells, the buoyant density of viral particles contained within conditioned medium was examined. FIG. 8 presents an analysis of viral particles produced by HepG2 cells infected with HBV baculovirus. Medium conditioned by HepG2 cells for 24 hours four days p.i. with 50 pfu HBV baculovirus/cell was analyzed by isopycnic centrifugation in a CsCl gradient followed by fractionation. (A) The density of each fraction is indicated as well as the amount of HBsAg present in selected fractions. (B) Fractions were also analyzed for DNA content by extraction of DNA and Southern blotting.

Figure 8A:
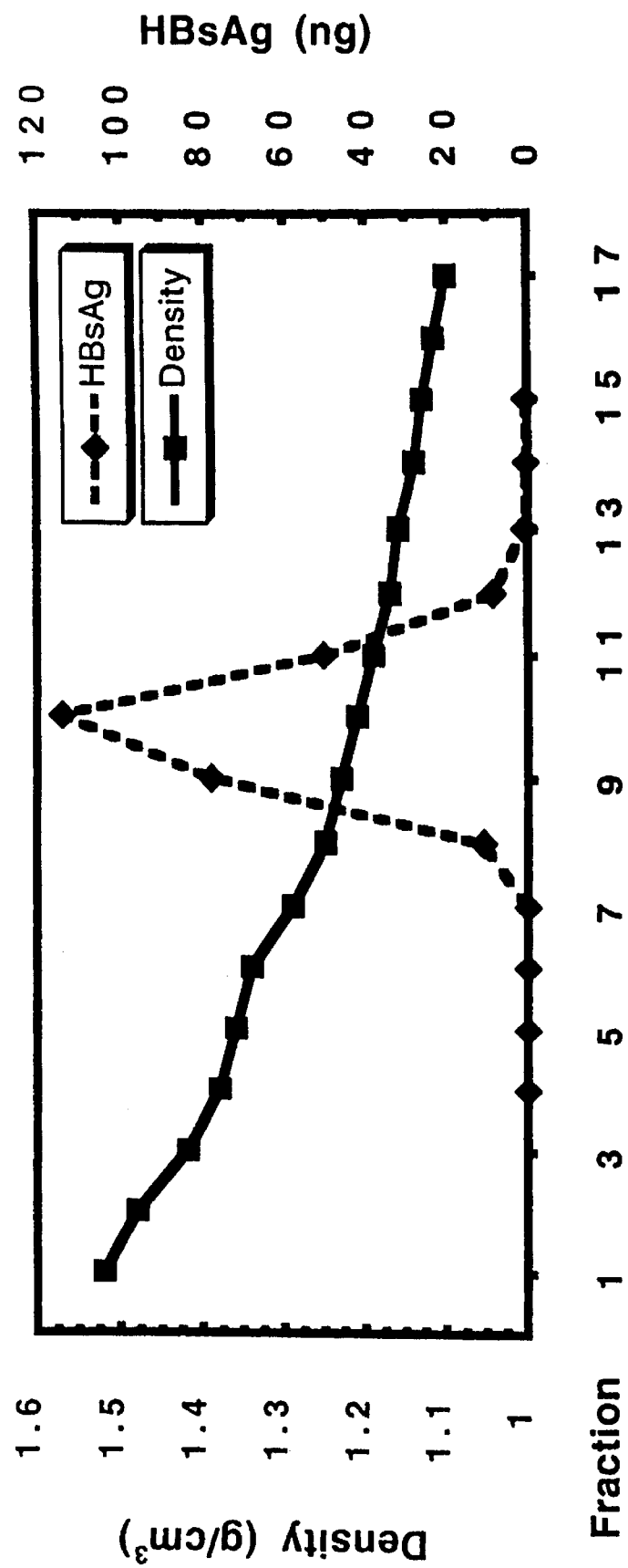
FIG. 8 presents an analysis of viral particles produced by HepG2 cells infected with HBV baculovirus.
Figure 8B:

HepG2 cells were infected with 50 pfu/cell and medium exposed to the cells for 24 hours was collected four days p.i. Conditioned medium was subjected to isopycnic density analysis in a CsCl gradient and the gradient was subsequently fractionated. The HBsAg and DNA content of fractions between the densities of 1.4 and 1.1 g/cm3 were determined (FIG. 8A and FIG. 8B). HBV DNA was detected at two distinct locations within the gradient. The majority of HBV DNA was found in fractions eight and nine which had densities of 1.25 and 1.23 g/cm3 respectively. The DNA in these fractions was almost exclusively composed of DS and RC forms of the HBV genome. Interestingly, the less dense fraction nine also contained trace amounts of lower molecular weight DNA of sizes consistent with HBV replicative intermediates. Minor amounts of HBV DNA were also found in fractions four and five which had densities of 1.38 and 1.36 g/cm3. Fraction four contained exclusively DS and RC forms of the HBV genome whereas DNA in the less dense fraction five was comprised of smaller species at sizes consistent with single and partially double-stranded HBV replicative intermediates. HBsAg analysis of the gradient indicated that HBV surface antigen was detected in fractions eight to twelve only (densities 1.25 to 1.17 g/cm3). The highest concentration of HBsAg was found in fraction ten (density 1.21 g/cm3). Results from HBsAg and DNA analyses of the gradient suggest that the DS and RC HBV DNA in fractions eight and nine are derived from enveloped Dane particles because HBsAg is present in these fractions and because HBV DNA and HBsAg comigrate at a density which has previously been reported for Dane particles. DNA detected in fractions four and five most likely indicates the presence of extracellular core particles lacking envelopes because these fractions are devoid of HBsAg. In addition, it has been previously reported that unenveloped core particles migrate to the same density. The high concentrations of HBsAg contained in fractions nine to twelve most likely represent HBsAg filaments and spheres which have been reported to migrate to these densities.

EXAMPLE 9

Time Course Analyses of Production of HBV Transcripts, Replicative Intermediates, CCC DNA, and Extracellular HBV DNA in HepG2 Cells Infected with HBV Baculovirus FIG. 9 shows a time course analysis of HBV RNA and DNA produced by HBV baculovirus infected HepG2 cells. HepG2 cells were seeded in 60-mm dishes and infected with 50 pfu HBV baculovirus/cell. On the indicated days p.i. cultures were harvested and analyzed for various HBV products. (A) Total RNA was extracted from one 60-mm dish and 10 $\mu$g were analyzed by Northern blotting. (B) The replicative intermediates present in one 60-mm dish were isolated and analyzed by Southern blotting. (C) The CCC DNA present in one 60-mm dish was isolated and analyzed by Southern blotting. (D) The amount of extracellular DNA present in the medium of one 60-mm plate was purified and analyzed by Southern blotting. Cultures were fed daily and the extracellular DNA detected represents DNA released into the medium over the 24-hour period before collection.

Figure 9A:
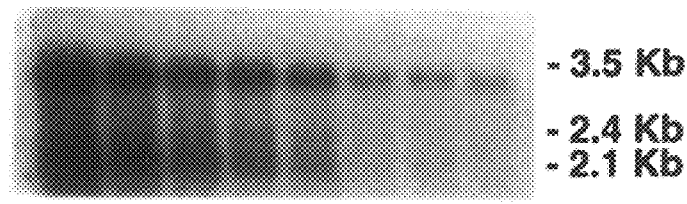
FIG. 9 shows a time course analysis of HBV RNA and DNA produced by HBV baculovirus infected HepG2 cells.

These studies were performed using HBV baculovirus at an moi of 50 pfu/cell. The 3.5-, 2.4-, and 2.1-kb HBV transcripts were readily detectable from day one to day eleven p.i. (FIG. 9A). All three HBV transcripts were most abundant one day p.i. and declined thereafter. This result was not surprising because equal amounts of RNA were analyzed at each time point. HepG2 cells were actively dividing throughout the time course and these results indicate that the relative amount of HBV RNA per cell decreased with time. The intensity of the 2.1-kb band was greater than the intensity of the 2.4-kb band throughout the eleven-day period.

Figure 9B:
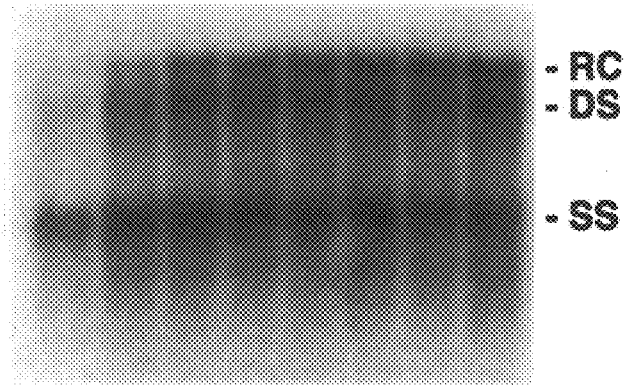

HBV replicative intermediates were expressed at high levels from day two to eleven p.i. Bands corresponding to SS and DS DNAs were detectable as early as one day p.i. (FIG. 9B). These results indicate that RNA encapsidation and reverse transcription occurred within one day of baculovirus infection. At one day p.i., the intensity of the band representing HBV SS DNA was considerably greater than the band representing HBV DS DNA. The difference in the ratio of SS to DS DNA between days one and two p.i. suggests that synthesis of the plus strand of the HBV genome required additional time, as might be expected. The total level of replicative intermediates present in the cultures remained remarkably constant over the eleven-day time course.

Figure 9C:
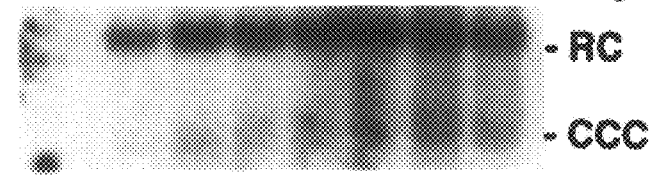

Time course analysis revealed that CCC HBV DNA was detectable from day two through day eleven p.i. (FIG. 9C). The fact that CCC DNA is not detectable in HepG2 on day one p.i. is most likely caused by the fact that very few core particles containing DS DNA are available to cycle back into the nuclei of infected cells at that time. Analysis of replicative intermediates indicated that intracellular cores containing DS DNA were present at higher concentrations on day two p.i, and at that time, CCC first became detectable. There was a small increase in the amount of CCC DNA as the time p.i. progressed.

Figure 9D:
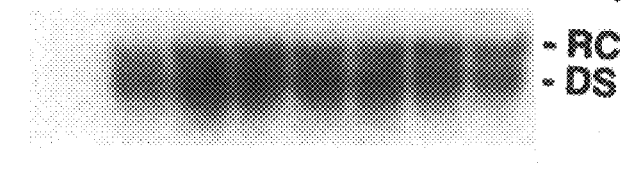
Figure 10A:
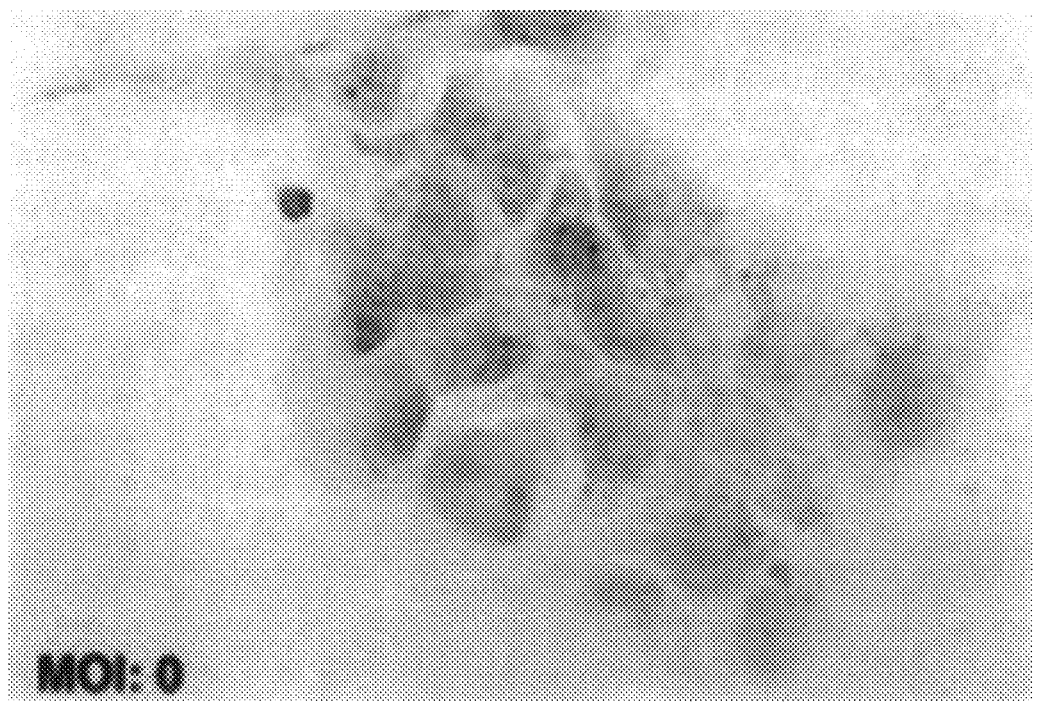
FIG. 10 presents an immunohistochemical analysis of HBcAg in HepG2 cells infected with HBV baculovirus.
Figure 10B:
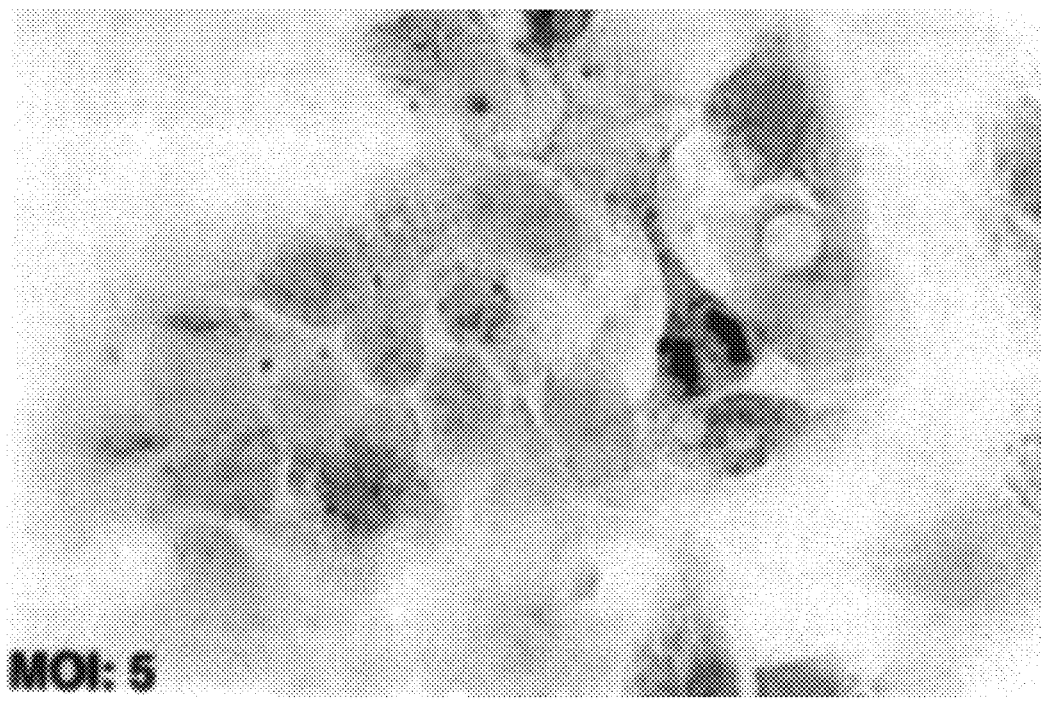
Figure 10C:
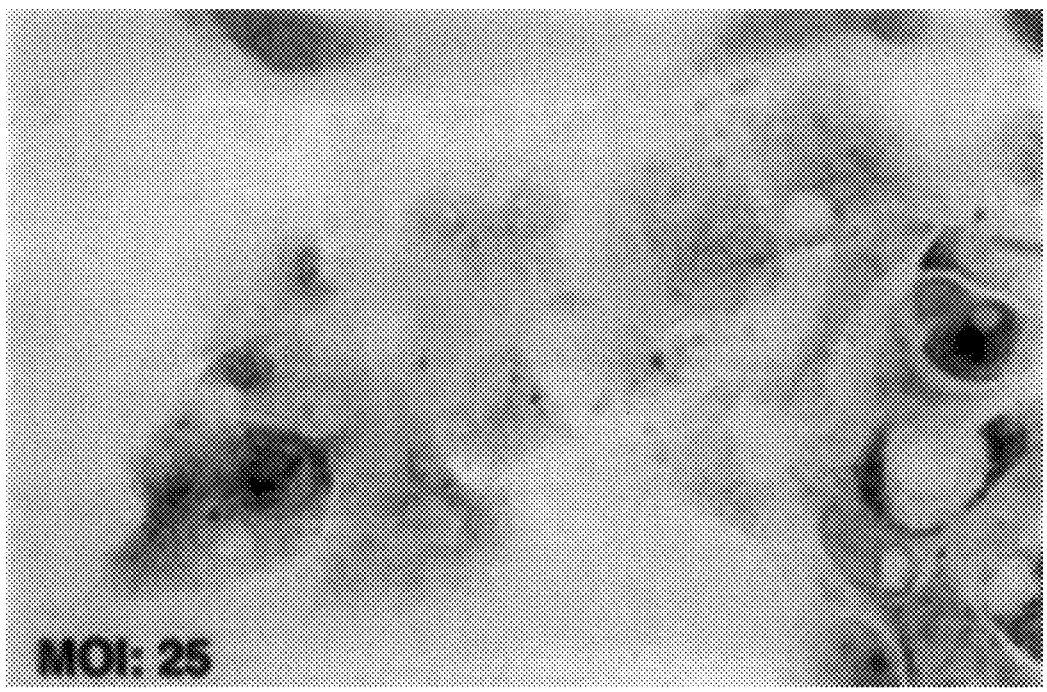
Figure 10D:
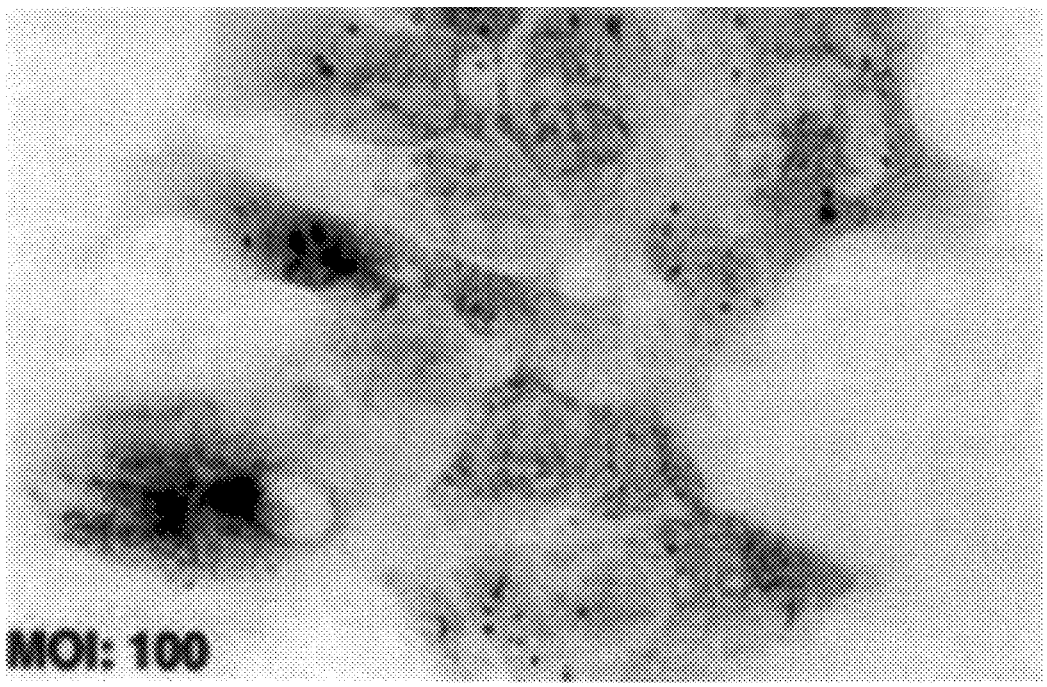

Time-course analysis of medium from HepG2 cells infected with HBV baculovirus indicated that extracellular virions were not detectable at one day p.i., but were easily detectable by two days p.i. (FIG. 9D). Based on the time course for synthesis of replicative intermediates and the finding that the majority of the intracellular cores had not completed second-strand synthesis at the end of day one p.i., virions would not be expected to be present in the medium one day p.i. Virions appeared in the medium on day two p.i., which was concurrent with appearance of intracellular cores containing DS DNA. The level of HBV virions in the medium was reasonably constant from three to nine days p.i. but diminished slightly at day eleven p.i. Because every 24 hours the medium was harvested for analysis and the cells were fed fresh medium, the bands in the Southern blot indicate the amount of extracellular virions that accumulate within a 24-hour period.

EXAMPLE 10

Immunohistochemical Analysis of HBcAg Expression

The expression pattern of HBcAg within populations of infected HepG2 cells was assayed by immunohistochemical staining. It has been previously reported using histochemical staining that 50% of HepG2 cells are capable of expressing Rous Sarcoma Virus promoter driven reporter genes following infection with recombinant baculoviruses. To determine the percentage of HepG2 cells capable of expressing HBV enhancer and promoter driven HBcAg expression following infection with recombinant baculoviruses, the expression pattern of HbcAg within populations of infected HepG2 cells was assayed by immunohistochemical staining. FIG. 10 presents an immunohistochemical analysis of HBcAg in HepG2 cells infected with HBV baculovirus. HepG2 cells were seeded in 100-mm dishes and infected the following day with 0, 5, 25, and 100 pfu/cell. Cells were fixed with zinc formalin 36 hours p.i. Core antigen staining was performed using anti-HBcAg primary antibody (1:700 dilution) and a horseradish peroxidase conjugated secondary antibody according to manufacturer's instructions. (Original magnification ×480.) Cells infected with HBV baculovirus at multiplicities of 0, 5, 25, and 100 pfu/cell were fixed approximately 36 hours p.i. HBcAg staining was carried out using an anti-HBcAg primary antibody and a horseradish peroxidase detection system. HBcAg was detectable in cells infected at all multiplicities, and staining intensity was proportional to moi (FIG. 10). HBcAg staining was strongest in the cytoplasm of infected cells; however, some nuclear staining was also apparent. At an moi of 100, strong HBcAg staining was detected in at least 75% to 85% of HepG2 cells. Below a moi of 100, staining intensity and the number of positive cells decreased proportionally with the moi.

EXAMPLE 11

Use of HBV Baculovirus to Mediate HBV Expression in the Huh-7 Cell Line.

Huh-7 is a hepatoma cell line derived from cancerous liver tissue removed from a 57-year old Japanese male with hepatocellular carcinoma. (Nakabayshi, et al., 1982) Huh-7 cells are considered well-differentiated because they have retained the expression of many liver-specific proteins. Several researchers have previously investigated the ability of Huh-7 to express and replicate hepatitis B virus (HBV) in vitro. Results of transient transfection of HBV DNA into Huh-7 cells using classical calcium phosphate procedures have indicated that the Huh-7 cell line is capable of transcribing HBV genes, synthesizing HBV antigens, and replicating the virus. Despite the observation that Huh-7 cells are able to replicate HBV, no Huh-7 derived stable HBV expressing cell lines have been reported to date.

Similar to HepG2 cells, Huh-7 cells can be efficiently transfected using the baculovirus as a vector. (Hoffman, et al., 1995) HBV baculovirus can mediate HBV expression in Huh-7 cells, as shown herein.

Figure 11:
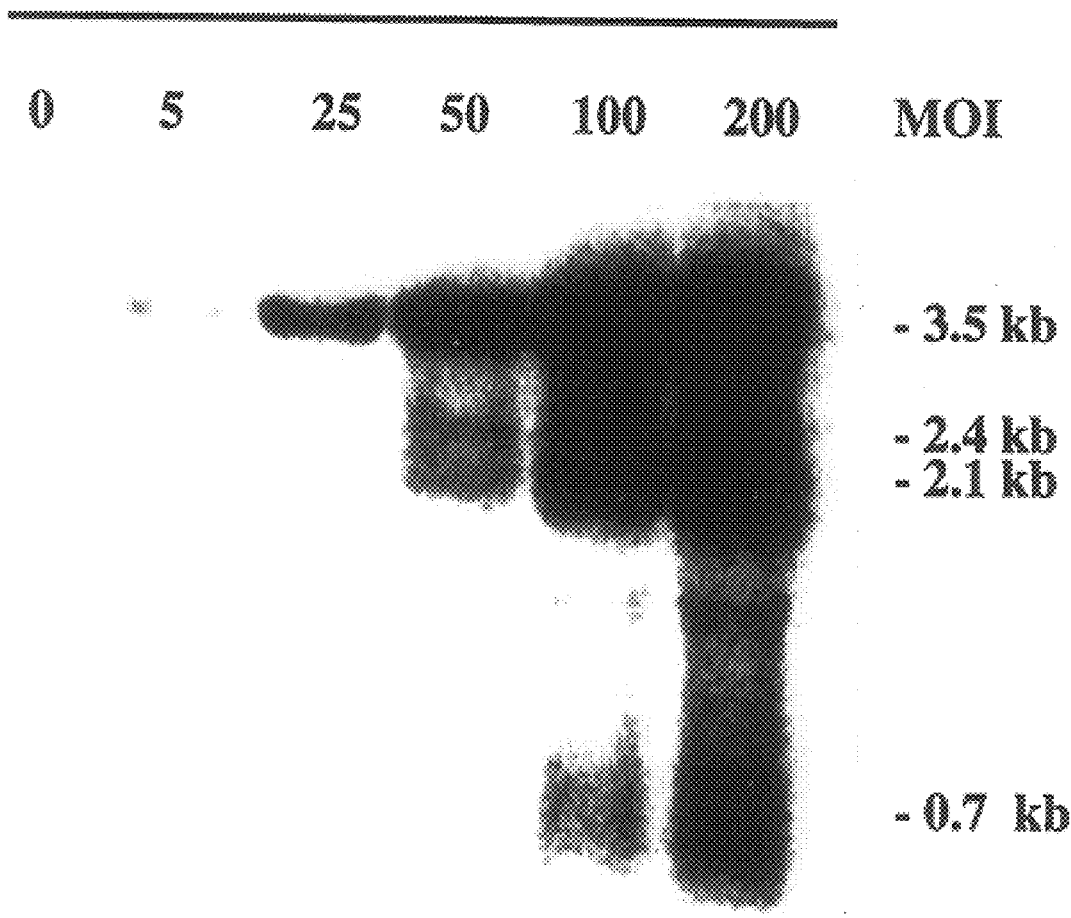
FIG. 11 shows an analysis of HBV transcripts produced in Huh-7 cells infected with HBV baculovirus.

Results of Northern blot analysis on RNA extracted from HBV baculovirus-infected Huh-7 cells indicate that the four HBV messages observed in vivo are also produced by Huh-7 cells after HBV baculovirus infection (FIG. 11). As previously observed with HBV baculvoirus-infected HepG2 cells, the level of HBV transcripts produced in infected Huh-7 cells is dependent on the dose of HBV baculovirus administered to the cells. HBV messages were observed when infecting Huh-7 with an moi as low as 5 pfu HBV baculovirus/cell (the least number of pfu tested); infection with higher multiplicites (50–200 pfu HBV baculovirus/cell) resulted in the strong expression of all four HBV messages.

Figure 12:
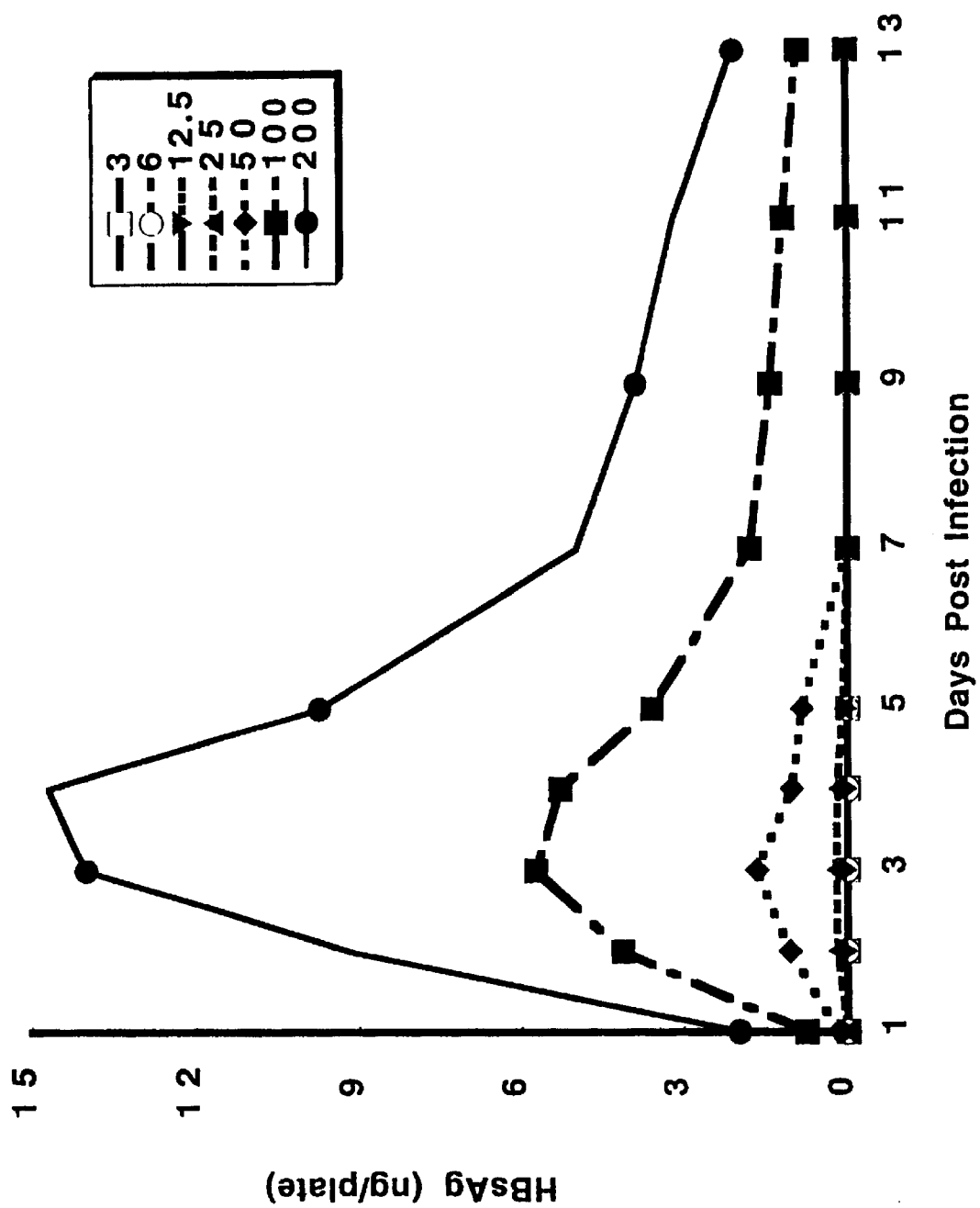
FIG. 12 shows a time course of HBsAg secretion by Huh-7 cells infected with HBV baculovirus.
Figure 13:
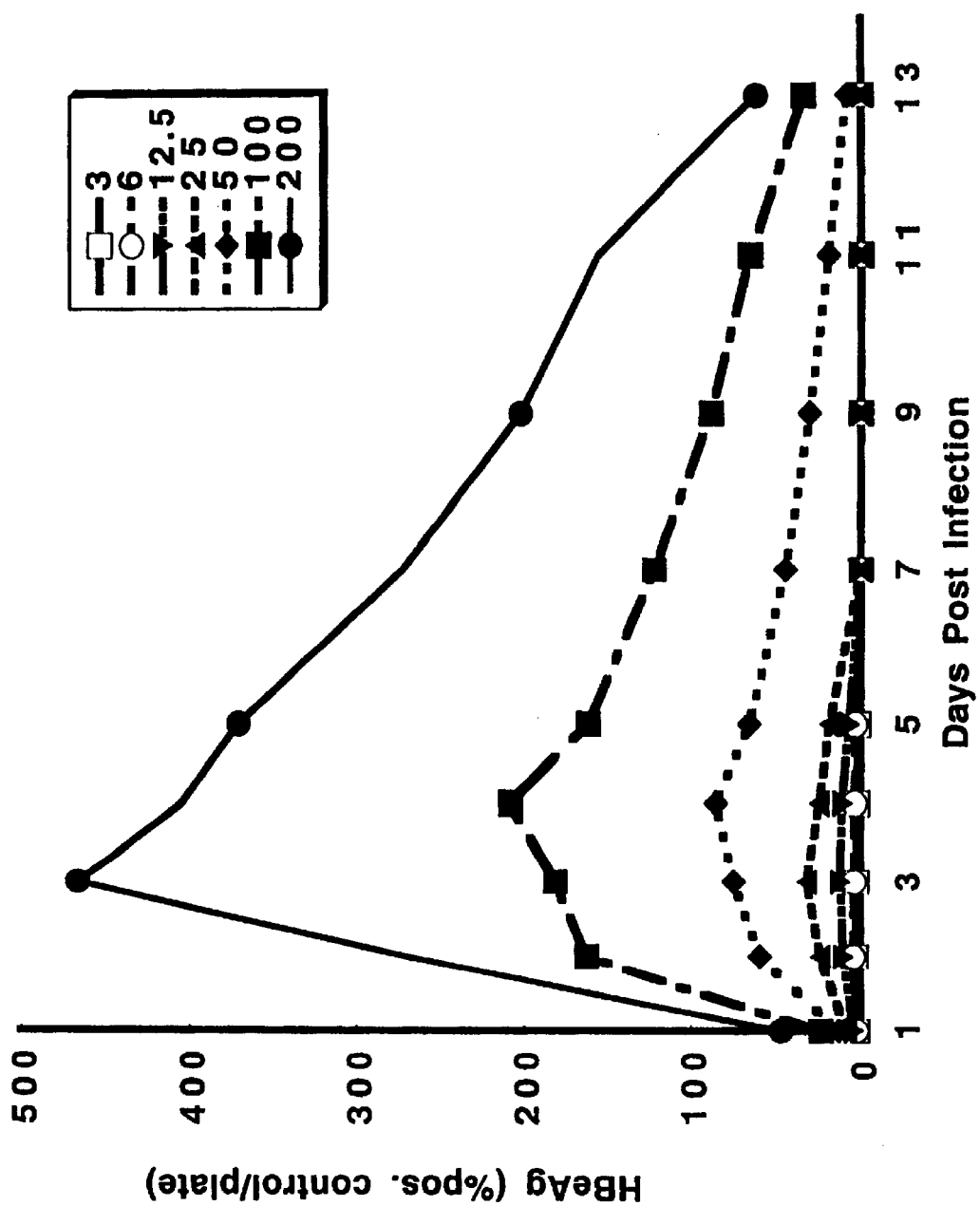
FIG. 13 shows a time course of HBeAg secretion by Huh-7 cells infected with HBV baculovirus.
Figure 14:
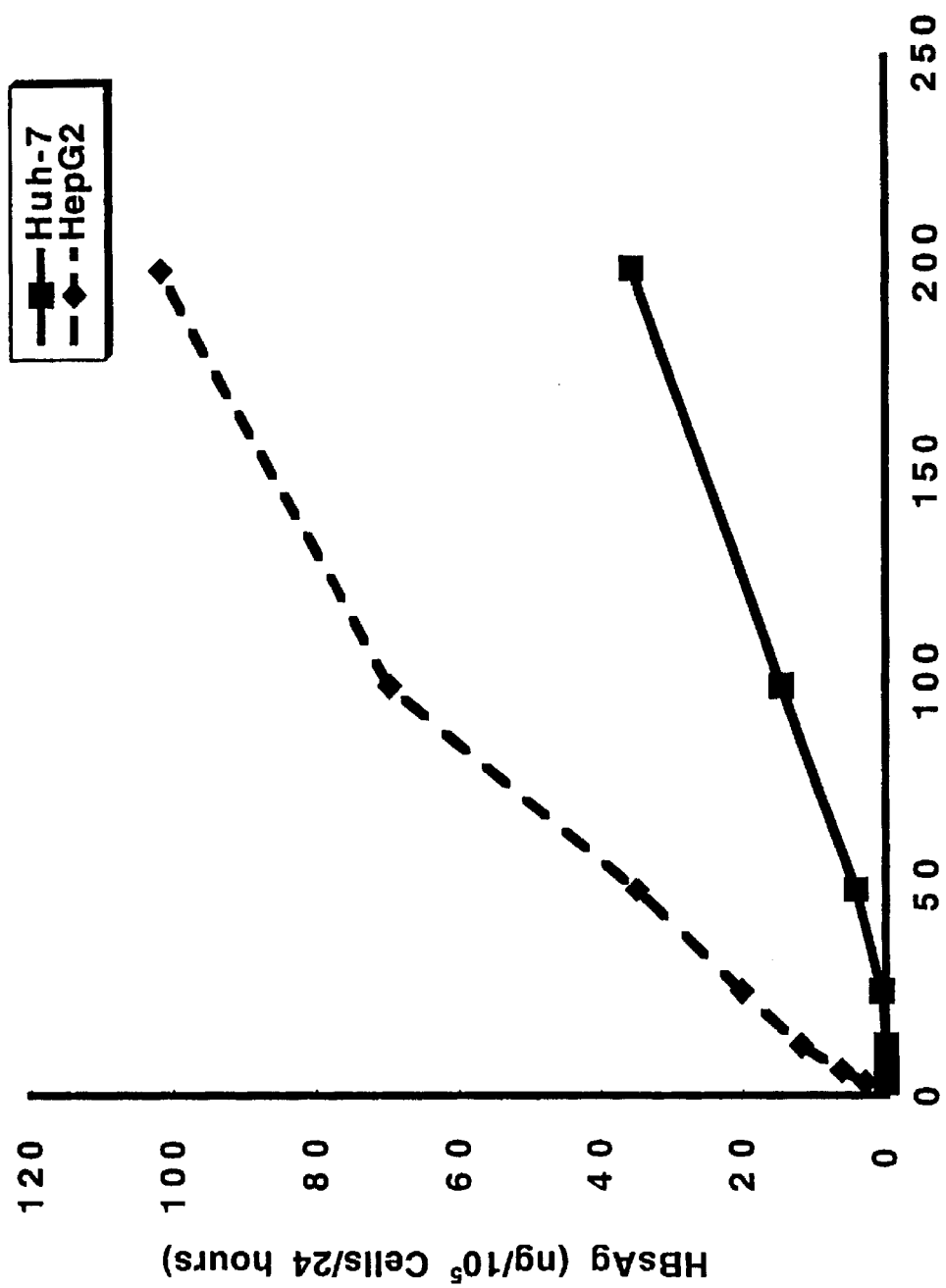
FIG. 14 shows comparative analyses of HBsAg in the medium of Huh-7 cells and HepG2 cells infected with HBV baculovirus.
Figure 15:
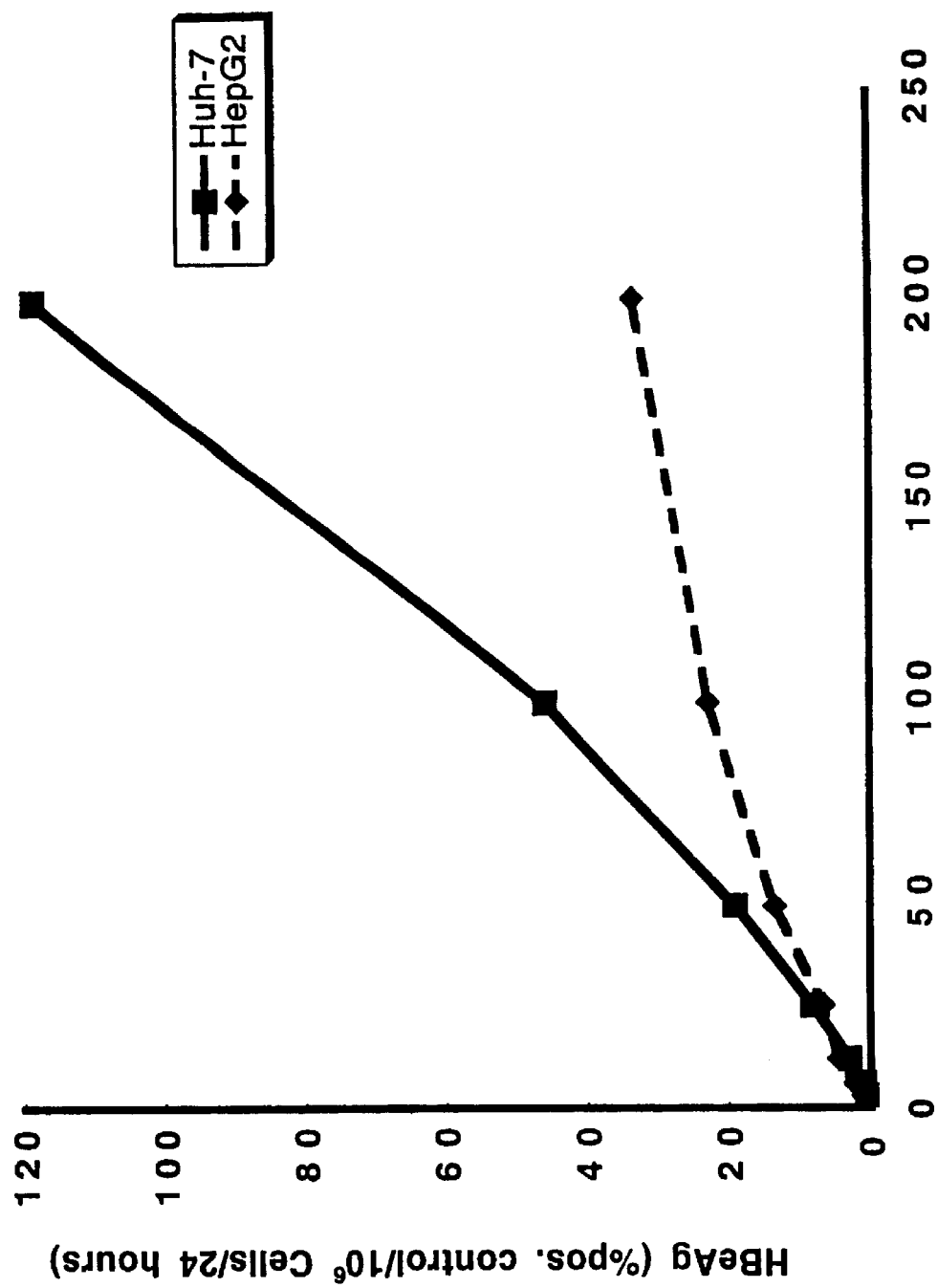
FIG. 15 shows comparative analyses of HBeAg in the medium of Huh-7 and HepG2 cells infected with HBV baculovirus.

Analyses of the secretion of HBV antigens by HBV baculovirus-infected Huh-7 cells indicated that both hepatitis B surface antigen (HBsAg) and hepatitis B surface antigen (HBeAg) are secreted from Huh-7 cells within 24 hours of baculovirus infection (FIG. 12 and FIG. 13). Similar to HBV baculvoirus-infected HepG2 cells, the level of HBsAg and HBeAg secreted by infected Huh-7 cells is dependent on the dose of HBV baculovirus administered to the cells. When infections were performed using high multiplicities of HBV baculovirus (100–200 pfu/cell), the expression of both HBsAg and HBeAg persisted for at least two weeks post infection. Direct comparative analyses of the secretion of HBsAg and HBeAg from Huh-7 and HepG2 infected with multiplicities of 3–200 pfu HBV baculovirus/cell indicated that the secretion of HBV antigens varies significantly between the two cell lines (FIG. 14 and FIG. 15). Huh-7 cells secrete higher levels of HBeAg relative to HepG2 cells; Conversely, HepG2 cells secrete much higher levels of HBsAg than Huh-7 cells.

These studies indicate that the infection of Huh-7 cells with HBV baculovirus results in the efficient expression of HBV mRNA and in the secretion of HBV antigens. HBV-baculovirus can therefore be used to study the expression HBV in vitro in Huh-7 cells with the same advantages as reported for HepG2 cells. The ability to use HBV baculovirus to study HBV in Huh-7 cells is particularly important because no HBV-expressing stable cell lines have been established in the Huh-7 background.

The observation that Huh-7 and HepG2 secrete significantly different amounts of HBeAg and HBsAg is an important finding; this indicates that the transcription of HBV genes and/or the intracellular processing of HBV proteins varies between these cell lines. Identifying the underlying basis for these differences may contribute to a greater understanding of HBV and its requirements for expression within the environment of the hepatocyte. The ability to use HBV baculovirus to infect both HepG2 and Huh-7 cells also allows HBV to be studied in two cell lines using a single, highly effective method of transfection. The use of two distinct hepatic cell lines to study HBV in vitro will aid in distinguishing between results which may be relevant in vivo and those which may be an artifact of a single cell line. HBV baculovirus-HepG2 cell system is well suited for studying antiviral compounds. Huh-7 cells are also suitable. Availability of multiple cell lines will enhance the ability to characterize the efficacy of antiviral compounds and will also be useful for molecular studies of HBV.

EXAMPLE 12

The Ability of HBV Baculovirus to Mediate HBV Expression in Primary Human and Rat Hepatocytes.

A. Detection of hepatitis B surface antigen secreted by primary human hepatocytes maintained in three distinct medium formulations.

Figure 16:
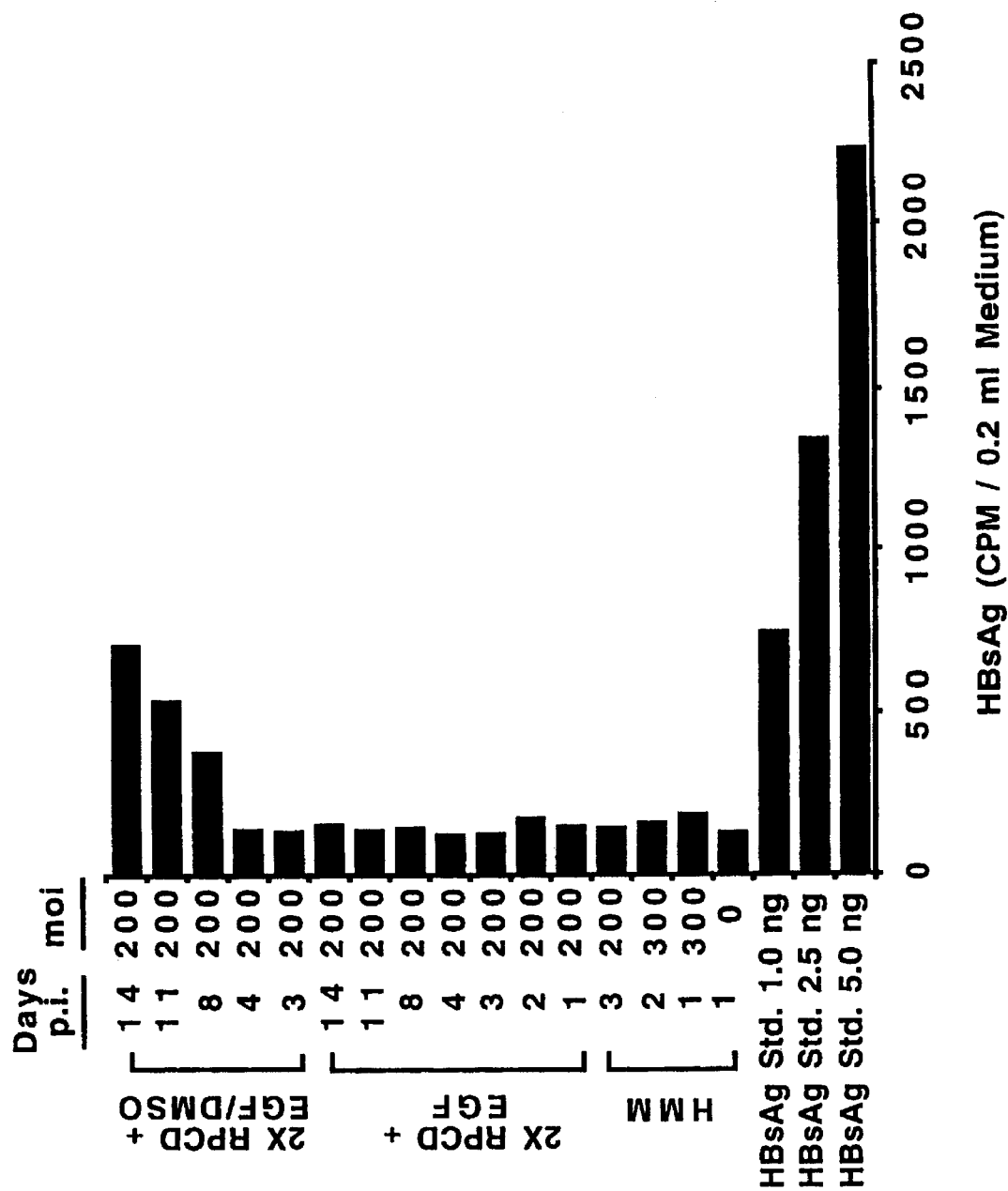
FIG. 16 shows an analysis of HBsAg secretion by primary human hepatocyles grown in various media for mutations and infected with HBV baculovirus.

Primary human hepatocytes seeded in 35-mm wells were purchased from Clonetics (Walkersville, Md.) and maintained in either Clonetics hepatocyte maintenance medium (HMM), 2× RPCD supplemented with epidermal growth factor (EGF), or 2× RPCD supplemented with EGF and dimethyl sulfoxide (DMSO). The morphological appearance of the human hepatocytes used in these studies indicated that the hepatocytes were modest in quality. One day post seeding, primary hepatocytes were infected with HBV baculovirus at the mois indicated herein using an estimated cell number of $5 \times 10^5$ cells/well. At the indicated number of days post infection, conditioned medium was collected from the cells and analyzed for HBsAg content by radioimmunoassay (FIG. 16). The cells were fed 1.5 ml medium/well and 0.2 ml of medium was analyzed in each assay.

Results indicated that primary human hepatocytes maintained in 2× RPCD+EGF/DMSO were susceptible to gene transfer using recombinant baculovirus and were capable of secreting HBsAg following infection with HBV baculovirus. Cells maintained in HMM or 2× RPCD+EGF did not secrete detectable levels of HBsAg following HBV baculovirus infection.

B. Detection of hepatitis B surface antigen secreted by primary human hepatocytes with respect to time post infection.

Figure 17:
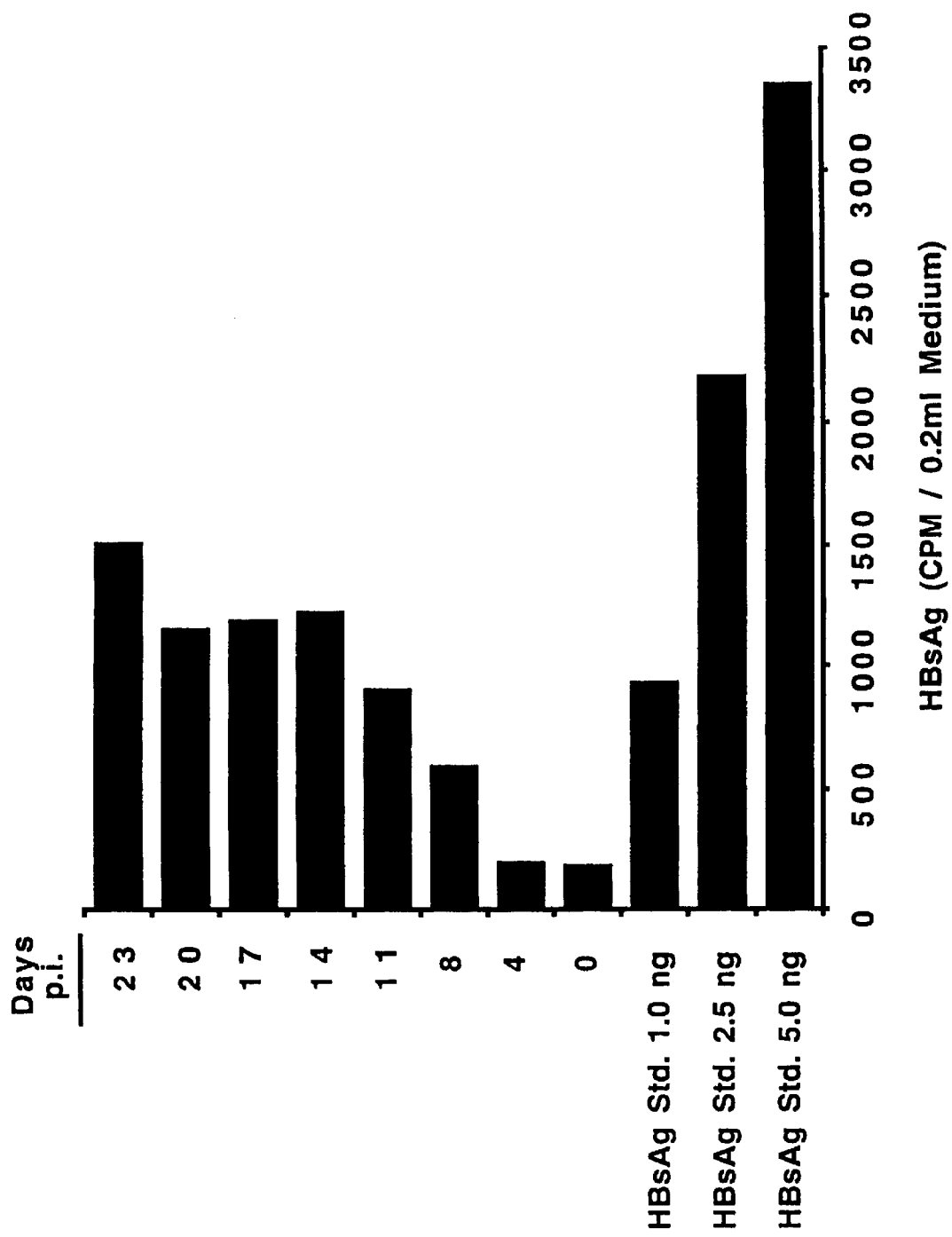
FIG. 17 shows a time course for HBsAg secretion by primary human hepatocytes infected with HBV baculovirus.

The same human hepatocyte cultures described above and fed 2× RPCD supplemented with EGF and DMSO continued to be examined for an additional nine days for production of HBsAg. Conditioned medium was collected from the cells and the newly collected samples as well as those that were collected up through day 14 were analyzed for HBsAg content by radioimmunoassay (FIG. 17). The expression of HBsAg increased with time in culture. It is important to note that the primary human hepatocytes did not replicate after plating. Non-dividing hepatocytes in vitro more closely resemble the in vivo conditions for HBV replication because hepatocytes in the intact human liver do not replicate.

C. Conclusions.

The data indicated that primary human hepatocytes infected with HBV recombinant baculovirus can produce HBsAg. Primary human hepatocytes maintained long-term in 2× RPCD+EGF/DMSO with HBV baculovirus may provide a method for studying HBV in a non-dividing population of primary human liver cells.

EXAMPLE 13

Effects of (-)-2'-dideoxy-3'-thiacytidine on Hepatitis B Virus Replication and Covalently Closed Circular DNA Amplification in HepG2 Cells Infected with Hepatitis B Virus Baculovirus (-)-2'-dideoxy-3'-thiacytidine (3TC, lamivudine) is a nucleoside analog which effectively interferes with the replication of HBV DNA in vitro and in vivo. The antiviral properties of 3TC in vitro were investigated in HepG2 cells infected with recombinant HBV baculovirus. FIG. 18 shows treatment schedules of HBV baculovirus infected HepG2 cells with 3TC prior to HBV RNA and DNA analyses. HepG2 cells infected with 50 pfu HBV baculovirus/cell were treated with several concentrations of 3TC and then analyzed for HBV RNA and DNA. Two treatment schedules were used for each concentration of 3TC tested: On the first schedule, indicated by T, 3TC treatment was initiated one day p.i. During the second schedule, indicated by P, 3TC treatment was initiated 16 hours prior to HBV baculovirus infection (pretreatment); in this group 3TC treatment was continued during and after infection. On the indicated days (3, 6, and 9 days of drug treatment) HBV replication in HepG2 cultures was assessed by examining extracellular HBV DNA and intracellular replicative intermediates. CCC HBV DNA and HBV transcripts were also analyzed after 3 and 6 days of 3TC treatment. Different types of information can be obtained using the HBV baculovirus-HepG2 system because (1) experiments can be carried out at varying levels of HBV replication including levels significantly higher than can be obtained from conventional HBV-expressing cell lines; (2) cultures can be manipulated and/or treated prior to or during the initiation of HBV expression; and (3) high levels of HBV replication allow the rapid detection of HBV products including covalently closed circular (CCC) HBV DNA from low numbers of HepG2 cells.

Figure 19A:
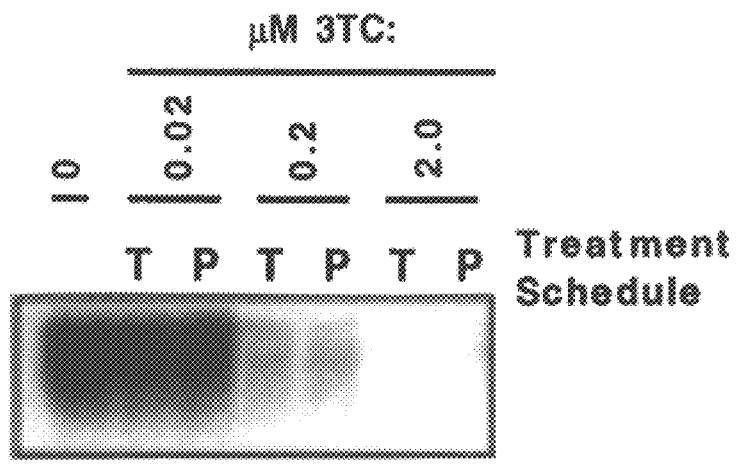
FIG. 19 shows the effect of 3TC treatment on HBV DNA secreted by HepG2 cells infected with 50 pfu HBV baculovirus/cell.
Figure 19B:
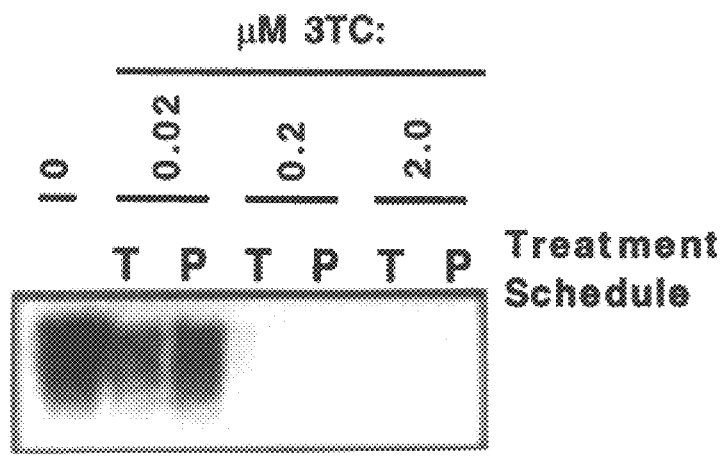
Figure 19C:
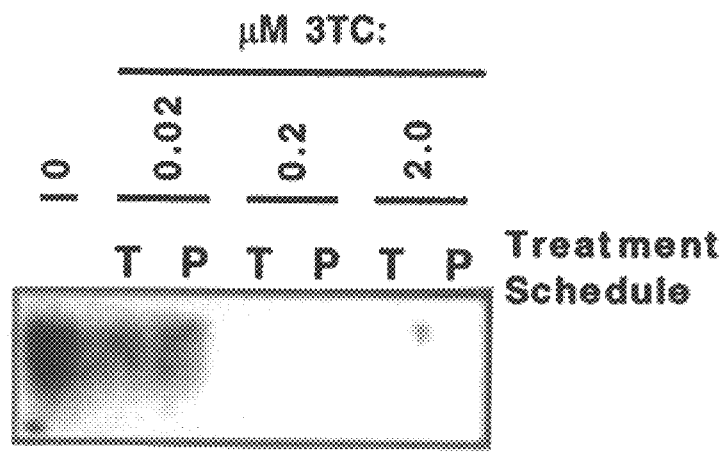
Figure 20A:
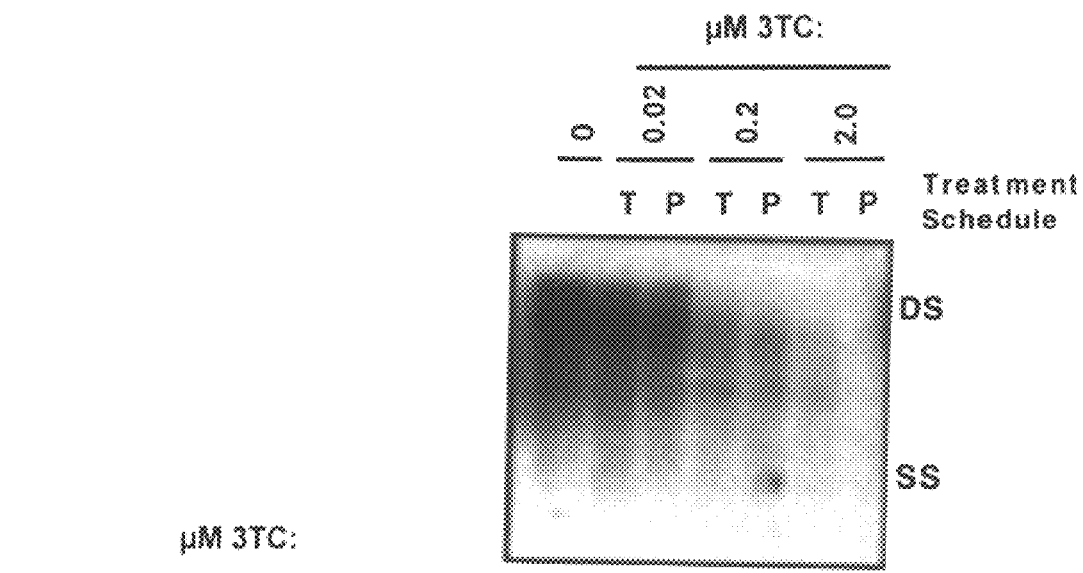
FIG. 20 shows the effect of 3TC treatment on HBV replicative intermediates in HepG2 cells infected with 50 pfu HBV baculovirus/cell.
Figure 20B:
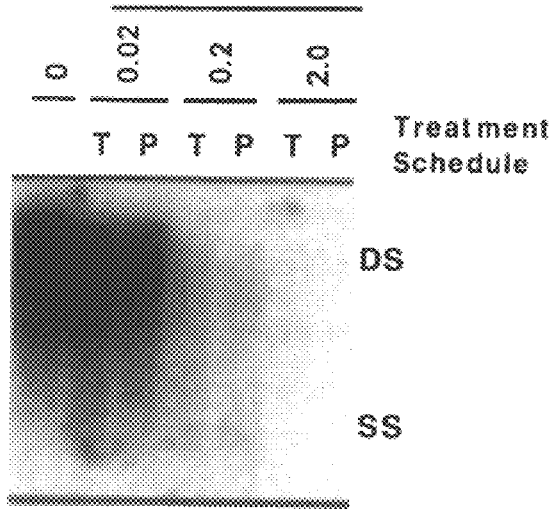
Figure 20C:
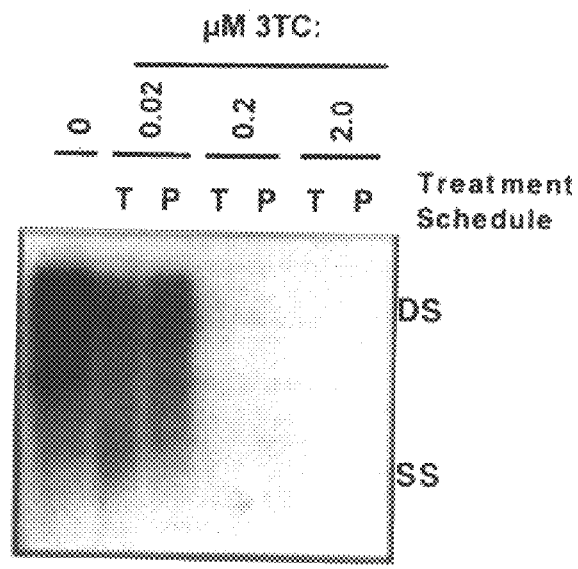

Treatment of HBV baculovirus infected HepG2 cells with 3TC resulted in an inhibition of HBV replication as evidenced by reductions in the levels of both extracellular HBV DNA and intracellular replicative intermediates. FIG. 19, Table 2 presents an analysis of HBV DNA secreted by HepG2 cells infected with 50 pfu HBV baculovirus/cell and treated with increasing concentrations of 3TC over a 10 day period. Treatments with 0, 0.02, 0.2, and 2.0 $\mu$M 3TC were initiated either 16 hours prior to HBV baculovirus infection (P) or 24 hours p.i. (T). After 3 (A), 6 (B), and 9 days (C) of 3TC treatment, DNA was extracted from the medium of each culture and analyzed by Southern Blotting. Relaxed circular (RC) and double-stranded (DS) forms of HBV DNA are indicated. FIG. 20, Table 3 is an analysis of HBV replicative intermediates in HepG2 cells infected with 50 pfu HBV baculovirus/cell and treated with increasing concentrations of 3TC over a 10 day period. Treatments with 0, 0.02, 0.2, and 2.0 $\mu$M 3TC were initiated either 16 hours prior to HBV baculovirus infection (P) or 24 hours p.i. (T). After 3 (A), 6 (B), and 9 days (C) of 3TC treatment, replicative intermediates were extracted from cytoplasmic core particles isolated from each culture. Replicative intermediates were analyzed by Southern blotting. Double-stranded (DS) and single-stranded (SS) forms of HBV genomic DNA are indicated. The effect of 3TC was both dose and time dependent and the reductions in extracellular HBV DNA agreed well with the reported efficacy of 3TC in vitro.

Figure 21A:
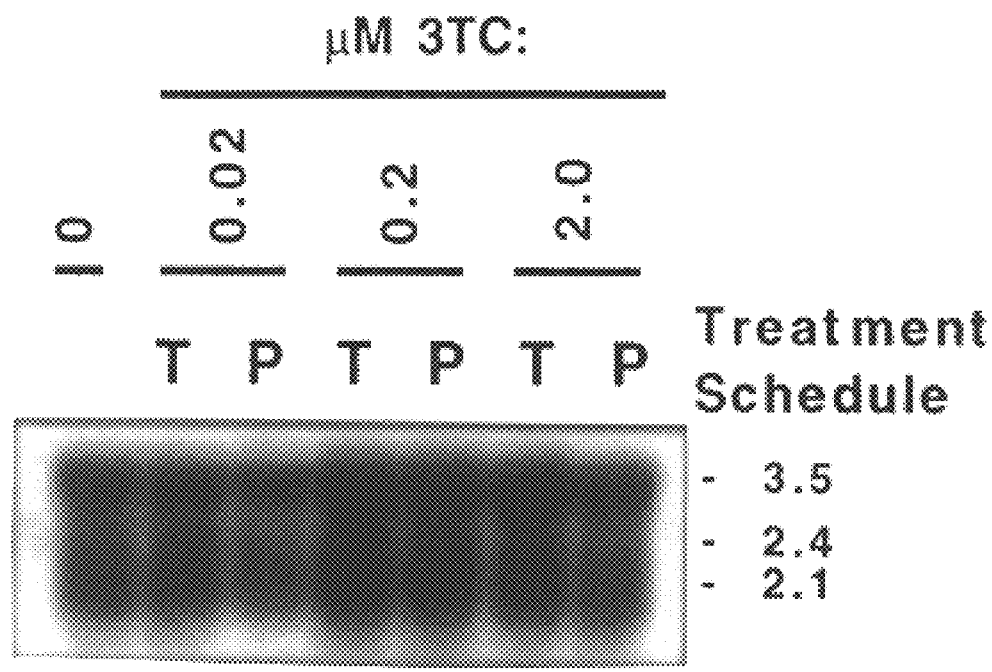
FIG. 21 shows the effect of 3TC treatment on HBV RNA transcripts produced by HepG2 cells infected with 50 pfu HBV baculovirus/cell.
Figure 21B:
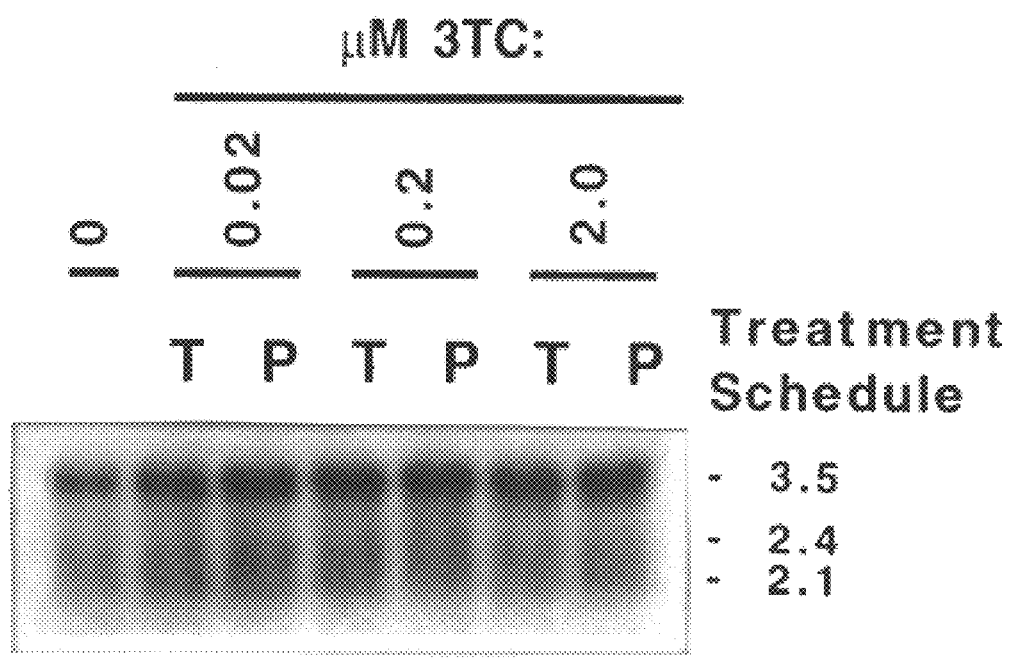
Figure 22A:
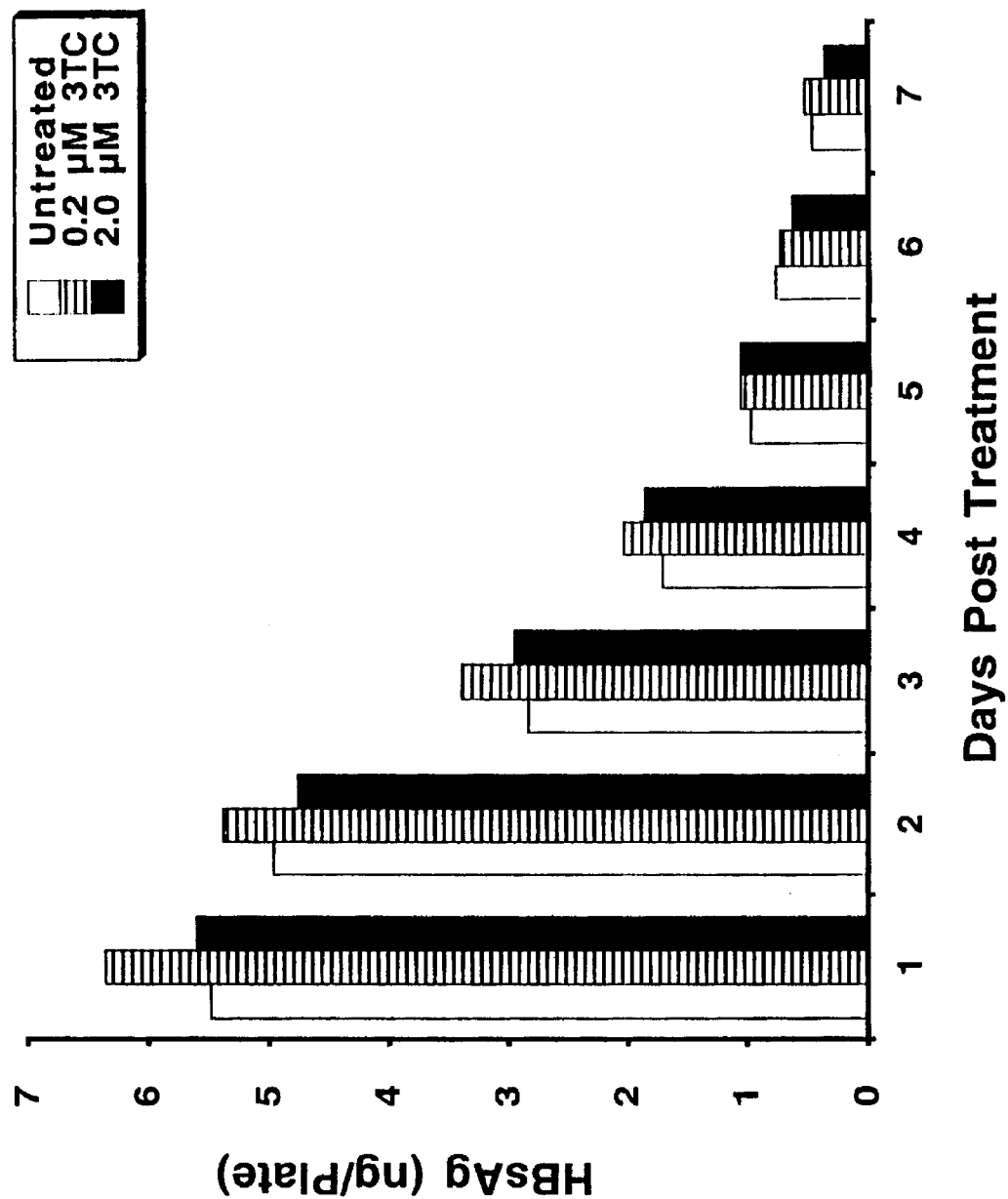
FIG. 22 presents an analysis on the effect of ETC treatment on HBV antigens secreted by HBV baculovirus infected HepG2 cells.
Figure 22B:
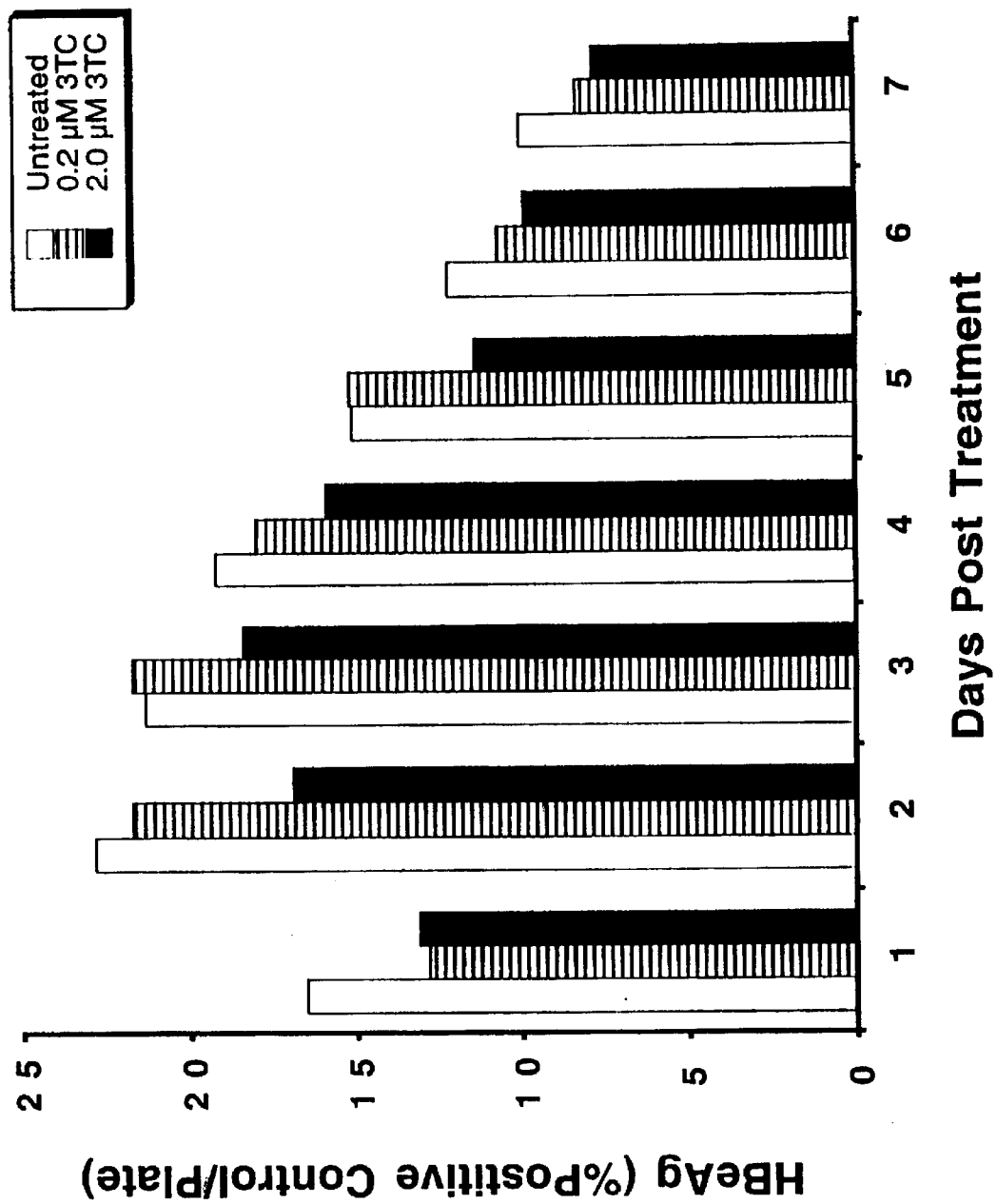
Figure 22C:
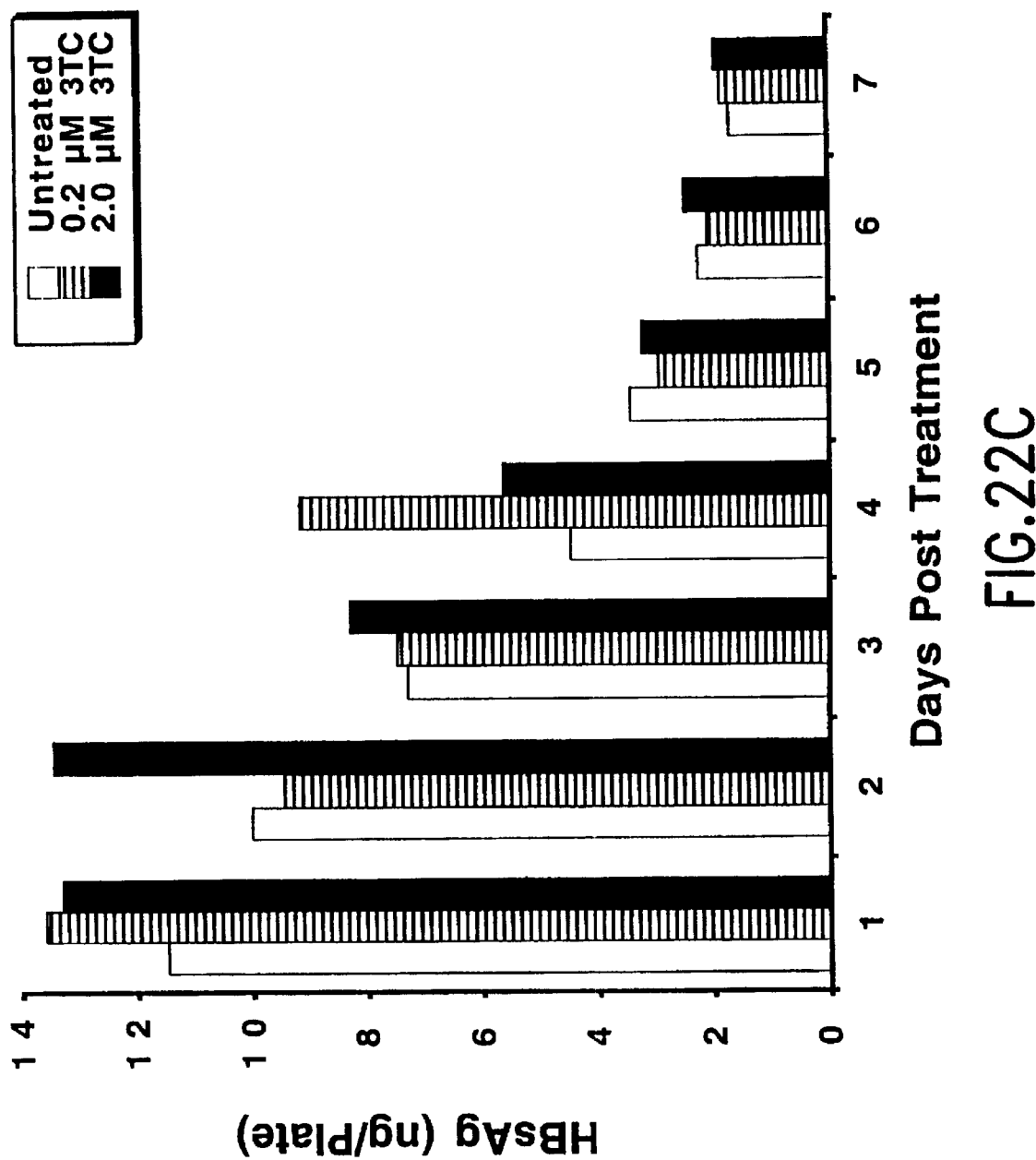
Figure 22D:
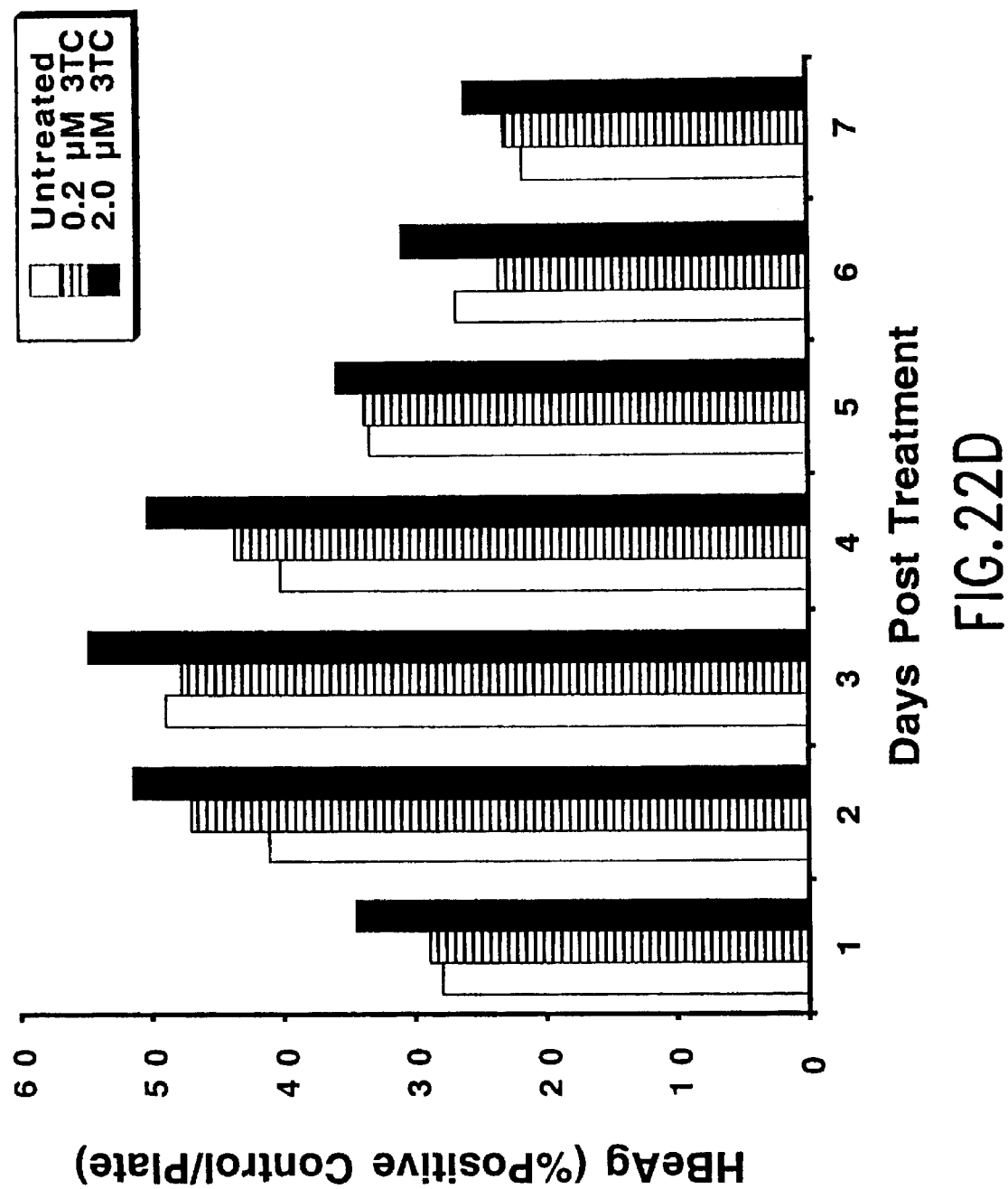

As expected, levels of HBV transcripts and extracellular HBsAg and HBeAg were not affected by 3TC. (FIGS. 21 and 22) FIG. 21 is an analysis of HBV transcripts in HepG2 cells infected with 50 pfu HBV baculovirus/cell and treated with increasing concentrations of 3TC over a 7 day period. Treatments with 0, 0.02, 0.2, and 2.0 $\mu$M 3TC were initiated either 16 prior to HBV baculovirus infection (P) or 24 hours p.i. (T). After 3 (A) and 6 (B) days of 3TC treatment, total RNA was harvested from cultures and 20 pg of total RNA was analyzed by northern blotting. The 3.5, 2.4 and 2.1 kb HBV transcripts are indicated. FIG. 22 is an analysis of HBV antigens secreted by HBV baculovirus infected HepG2 cells after a one week treatment with 3TC. HepG2 cells were infected with either 25 (A and B) or 50 (C and D) pfu HBV baculovirus/cell and were untreated (■), or treated daily with 0.2 (■) or 2.0 (■), $\mu$M 3TC starting 24 hours p.i. Conditioned medium was collected from each culture for one week and was analyzed for HBsAg (A and C) or HbeAg (B and D) content by radioimmunoassay.

Figure 23A:
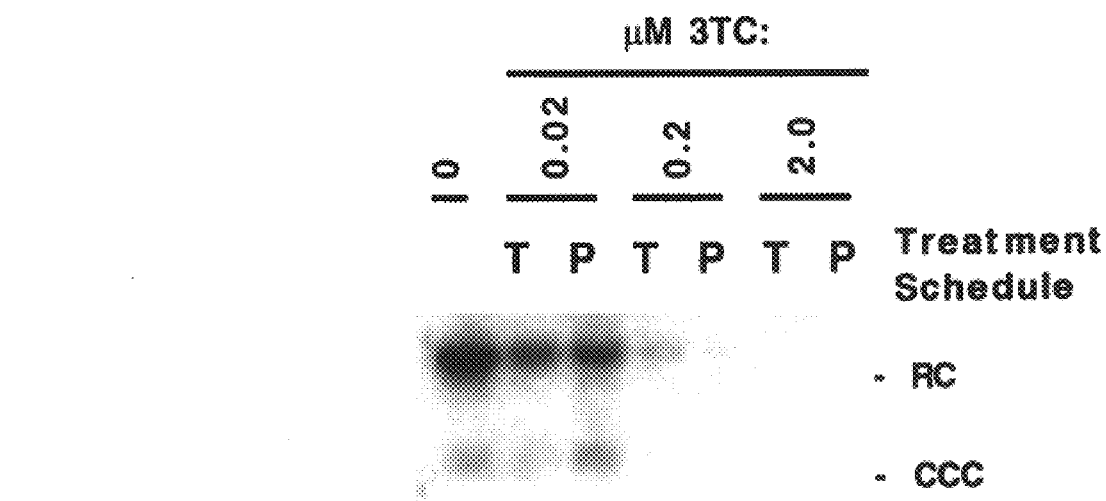
FIG. 23 shows the effect of 3TC treatment on HBV CCC DNA produced by HepG2 cells infected with 50 pfu HBV baculovirus/cell.
Figure 23B:
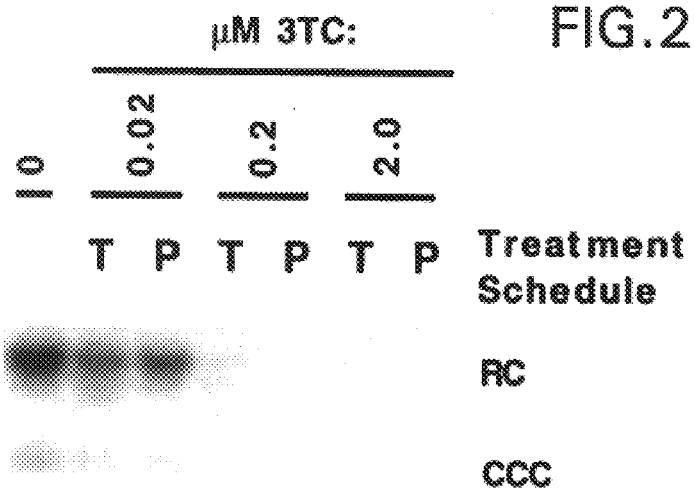
Figure 23C:
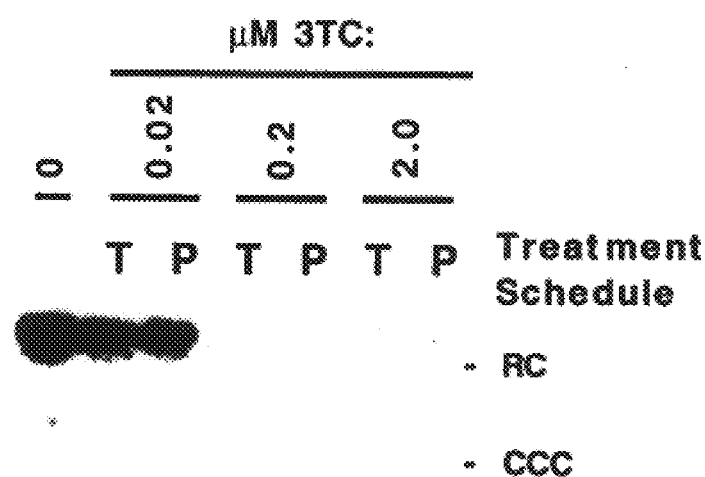
Figure 24A:
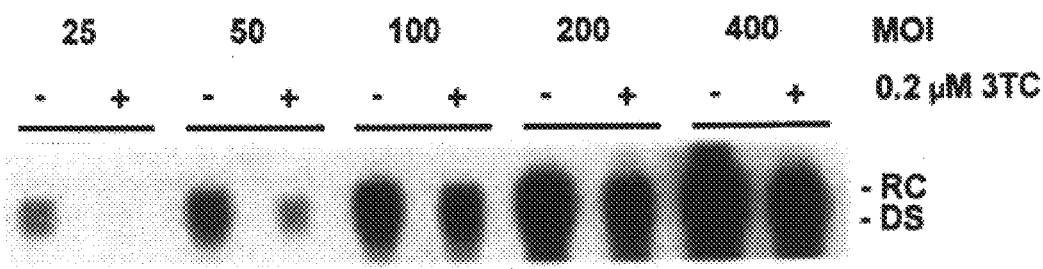
FIG. 24 shows the effect of 0.2 $\mu$M 3TC treatment on the HBV DNA content of medium from HepG2 cells expressing increasing levels of HBV.
Figure 24B:
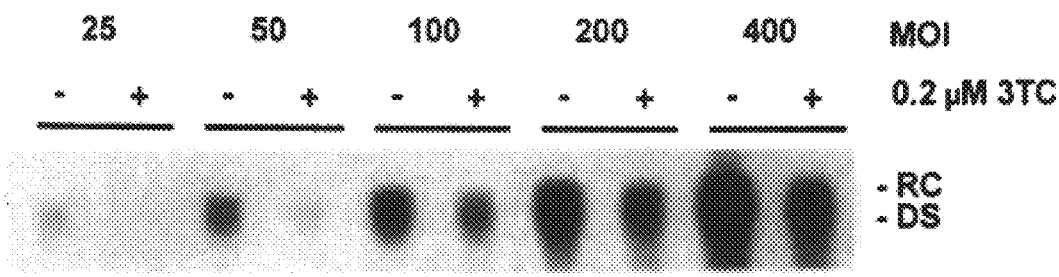
Figure 24C:
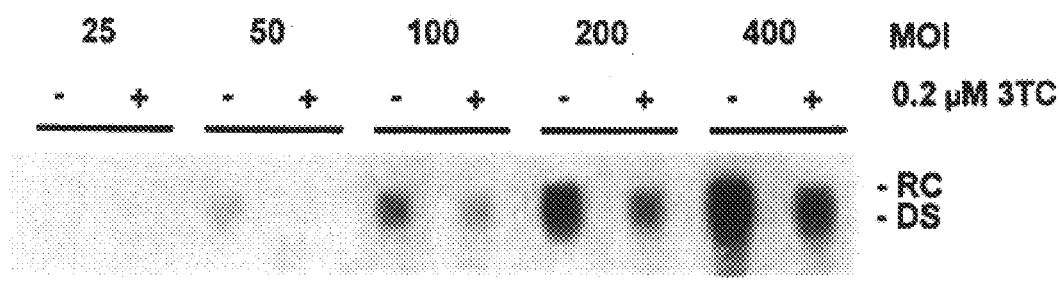
Figure 24D:
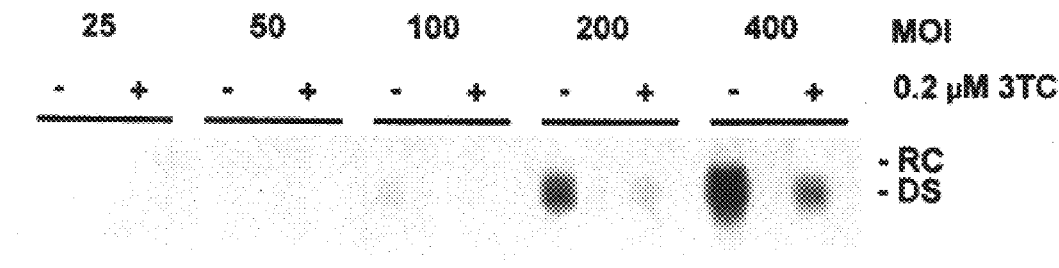

Importantly, the HBV baculovirus-HepG2 system made it possible to observe for the first time that 3TC treatment causes a large reduction in the amount of CCC HBV DNA that accumulates during HBV replication. (FIG. 23, Table 4) FIG. 23 is an analysis of CCC HBV DNA produced in HepG2 cells infected with 50 pfu HBV baculovirus/cell and treated with increasing concentrations of 3TC over a 10 day period. Treatments with 0, 0.02, 0.2, and 2.0 $\mu$M 3TC were initiated either 16 hours prior to HBV baculovirus infection (P) or 24 hours p.i. (T). After 3 (A) and 6 (B) days of 3TC treatment, non protein-associated DNA was extracted from each culture and analyzed by Southern blotting. Relaxed circular (RC) and covalently closed circular (CCC) HBV DNA is indicated. Treatment of HepG2 cells prior to HBV baculovirus infection resulted in a slight increase in the efficacy of 3TC compared to treatments starting 24 hours post infection. A conclusion from these studies is that the HBV baculovirus-HepG2 system can be used to complement other in vitro model systems currently used for testing antiviral compounds.

(-)-2'-dideoxy-3'-thiacytidine (3TC, lamivudine) is a nucleoside analog originally described as an agent capable of inhibiting the replication of type 1 and type 2 human immunodeficiency virus (HIV). It was subsequently reported that 3TC was also effective at inhibiting HBV replication in vitro and at reducing the level of serum HBV DNA in vivo in some animal models. 3TC is currently undergoing clinical trials and initial results have been promising. Treatment with 3TC is reported to be well-tolerated and effective at reducing or clearing HBV DNA from the serum of patients. A major drawback to 3TC therapy is that cessation of drug treatment results in the rapid reappearance of serum HBV DNA. The reason for this rebound is postulated to be the persistence of a covalently closed circular (CCC) form of the HBV genome which resides in the nuclei of infected hepatocytes. Although replicative forms of HBV DNA can be prematurely terminated by the incorporation of 3TC, there is little or no evidence to suggest that CCC DNA levels can be affected by treatment with 3TC or other nucleoside analogs. On the contrary, Moraleda et. al. (1997) have reported that established pools of Woodchuck Hepatitis Virus (WHV) CCC DNA produced in vitro in primary woodchuck hepatocytes are quite resistant to 3TC treatment. Recently, 3TC has also been used as a prophylactic agent during orthotopic liver transplant when HBV reinfection is a risk. Short term results from these trials indicate that 3TC suppresses HBV DNA production by the donor liver in some patients; however, the prevention of reinfection and long term efficacy has yet to be determined. It is unknown if preemptive treatment with nucleosides such as 3TC prior to transplant would be sufficient to prevent the accumulation of CCC HBV DNA in new liver tissue and potential reactivation of the virus.

The HBV baculovirus-HepG2 cell system also allows the detection of CCC HBV DNA which can be difficult to detect or undetectable in stably transfected HBV expressing cell lines such as HepG2 2.2.15 and HB611. Unlike stable cell lines, the time of infection can also be controlled allowing the manipulation or treatment of cells prior to or during the initiation of HBV expression. The primary goals of the studies described here were: (1) to evaluate the utility of the HBV baculovirus-HepG2 system as a tool for antiviral research using 3TC, an established inhibitor of HBV replication; (2) to provide further data on the in vitro efficacy of 3TC by investigating its effects on various levels of HBV replication; and (3) to examine the effect of administering 3TC prior to the initiation of HBV expression on viral replication and the accumulation of CCC HBV DNA.

The purpose of the study reported in this example was twofold: to explore the use of the HBV baculovirus HepG2 system for in vitro testing of antivirals and to further characterize the antiviral properties of the cytosine analog 3TC.

When testing viral mRNA synthesis and HBV antigen secretion by HBV baculovirus infected HepG2 cells, no differences were found between treated and untreated cultures. (FIGS. 21 and 22) This has also been reported by other investigators and is not unexpected based on the mechanism by which 3TC acts. 3TC is phosphorylated inside cells and is subsequently incorporated into nascent viral DNA by the HBV polymerase during replication. 3TC incorporation results in the termination of DNA elongation by virtue of its dideoxy structure. Therefore, the respected result would be that 3TC would not directly affect the transcription or translation of HBV gene products from nuclear DNA because it acts downstream of these events. It is interesting that an almost complete inhibition of the presence of extracellular HBV DNA did not result in any discernible alteration in the trafficking or secretion of HBeAg or HBsAg in HepG2 cells. This effect is also observed in patients, the majority of whom do not clear either HBeAg or HBsAg after long term treatment with 3TC even though their serum HBV DNA levels are markedly reduced.

When the effects of increasing 3TC concentration and treatment time on a single level of HBV replication (an moi of 50 pfu/cell) were measured, both HBV DNA synthesis and the secretion of virions into the medium were found to be highly sensitive to 3TC. (FIGS. 19 and 20) Extracellular HBV DNA could be reduced by more than 99% after nine days of treatment with 2.0 $\mu$M 3TC. Intracellular replicative forms of the HBV genome were only slightly less sensitive to inhibition than extracellular DNA at equal 3TC concentrations and treatment times; however, it should be noted that many of the intracellular HBV DNA molecules detected at high 3TC concentration were single-stranded. The accumulation of single-stranded HBV DNA suggests that many replicating genomes incorporated 3TC and were blocked from fully elongating into mature double-stranded genomes. Pretreatment of cells with 2.0 $\mu$M 3TC 16 hours before HBV baculovirus infection resulted in a small but consistent reduction in the levels of replicative intermediates and extracellular HBV DNA beyond what was observed when 3TC treatment was initiated 24 hours p.i. The effects of pretreatment were most evident at the earliest time points tested; little or no effects were observed after six and nine days.

The data presented here agree well with published studies on the efficacy of 3TC in vitro. (Kruining, et al. 1995) After treating HepG2 2.2.15 cells for 12 days, Doong et al., (1991) and Kruining et al., (1995) reported a 50% reduction of extracellular HBV DNA at concentrations of 0.05 and 0.02 $\mu$M 3TC, respectively. A nine day treatment with 0.02 $\mu$M 3TC resulted in a 67% reduction of extracellular HBV DNA produced by HepG2 cells infected at an moi of 50 pfu HBV baculovirus/cell. (Table 2) Analysis of earlier time points indicated that the decrease in extracellular HBV DNA was dependent on time; after only three days of treatment HBV DNA in the medium was reduced by only about 30%. Korba, (1996) reported that treatment with a concentration of 0.222 $\mu$M 3TC resulted in a 90% decrease in virion DNA produced by HepG2 2.2.15 after nine days of treatment. Similarly, about a 98% reduction in extracellular DNA was found after a 10 day treatment of HBV baculovirus infected HepG2 cells with 0.2 $\mu$M 3TC. Two important distinctions must be made between the 2.2.15 cell line used by other investigators and the HBV baculovirus-HepG2 system reported herein. First, at an moi of 50 pfu HBV baculovirus/cell, HepG2 cells produce much higher levels of HBV expression and replication than 2.2.15 cells. Second, with the exception of the appearance of CCC DNA, the copy number of HBV transcriptional templates per culture does not increase with time after HBV baculovirus infection. This is in contrast to cell lines containing integrated HBV genomes which double the number of transcriptional templates per culture each time the cells divide. Bearing these differences in mind, the results obtained by using stable cell lines and HBV baculovirus-HepG2 system are remarkably similar.

Analysis of non protein-associated RC and CCC forms of the HBV genome revealed that in addition to replicative intermediates and extracellular HBV DNA, the amplifcation of CCC DNA also can be affected by 3TC in a dose dependent manner. A greater than 90% inhibition of non protein-associated RC HBV DNA production by HepG2 cells treated with 2.0 $\mu$M 3TC occurred. (Table 4) Moraleda et al. (1997) reported that 2.0 $\mu$M 3TC was not effective at reducing established pools of WHV CCC DNA in primary woodchuck hepatocytes; however, they did observe an 80% inhibition of CCC WHV DNA amplification in primary woodchuck hepatocytes treated with 3TC prior to infection with WHV. The greater inhibition may be due to differences in either 3TC metabolism or the efficiency of CCC DNA formation between woodchuck hepatocytes and HepG2 cells.

During hepadnaviral replication, CCC HBV DNA can be produced by two pathways: 1) The entry of exogenous Dane particles into naive cells followed by migration of HBV cores to nuclei or 2) The cycling of newly synthesized progeny core particles from the cytoplasm of infected cells back to the nuclei. Once a core particle reaches the nucleus by either pathway, the HBV genome gains access to the nucleus by an unknown mechanism, is repaired to form RC DNA and is subsequently supercoiled into CCC DNA. The first pathway cannot be evaluated using the HBV baculovirus-HepG2 system or by using any cell lines because HBV does not directly infect cultured hepatocyte cell lines. The second pathway, however, can be evaluated by experiments carried out in this study. The cycling of mature core particles back to the nucleus appears to require the completion of second strand synthesis, as would be expected. 3TC interferes with the synthesis of viral DNA within immature core particles and effectively reduces the pool of mature core particles available to become mature enveloped virions or to cycle back to the nucleus to form RC/CCC DNA. It is also possible that 3TC could interfere with the nuclear repair of mature partially double-stranded HBV genomes into RC DNA. However, this repair is most likely carried out by host polymerases which are not sensitive to the concentrations of 3TC used in these experiments.

Unlike replicative intermediates and extracellular HBV DNA which were progressively inhibited with increasing time of 3TC treatment, RC and CCC DNA did not undergo a consistent decrease relative to control levels as the length of time of 3TC treatment increased. This finding suggests that 1) CCC HBV DNA, after formation, is fairly stable within the nuclei of infected HepG2 cells, and/or 2) Mature core particles can cycle back to the nucleus to offset CCC DNA turnover and maintain a small pool of episomal HBV genomes, even when HBV DNA replication was drastically suppressed as evidenced by the levels of extracellular HBV DNA and HBV replicative intermediates. If the later hypothesis is correct, it is possible that when very few mature HBV cores are present in the cytoplasm, there is a tendency for those cores to enter the CCC amplification pathway instead of acquiring an envelope and exiting the cell. Indeed, the finding that extracellular HBV DNA levels are suppressed to a greater extent than intracellular replicative intermediates provides support for this hypothesis. This would not be unlike the early stages of hepadnaviral replication when the initial cores produced after infection are believed to cycle back to the nucleus to allow an amplification of CCC DNA before the secretion of virions takes place.

The initiation of 3TC treatment in HBV positive patients receiving orthotopic liver transplants prior to transplantation may have short term benefits. First, administering 3TC before surgery should markedly lower the level of circulating virions capable of infecting new liver tissue. Second, in new hepatocytes which do become infected, a sufficient dose of 3TC may block or at least delay the onset of CCC DNA amplification by suppressing HBV replication. Depending on the stability of CCC DNA formed following infection, it is likely that some amplification will occur, albeit at a reduced rate, in 3TC treated cells. Although it is unlikely that 3TC alone could prevent liver reinfection, it is possible that continual treatment with sufficient doses may result in a significant delay in the accumulation of CCC DNA within new tissue. Ultimately, a cure for HBV will likely require the elucidation of a method for eliminating episomal HBV DNA in the nucleus of infected cells. Whether this can be accomplished by an exogenous agent, or by the induction of an existing cellular pathway remains to be seen. Although the initial formation of CCC HBV DNA due to viral entry cannot be prevented by 3TC, the amplification of CCC DNA could potentially be blocked or delayed sufficiently to increase the efficacy of other antiviral agents.

One limitation of using stable cell lines, such as HepG2 2.2.15 cells, for evaluating the efficacy of an antiviral on HBV replication is that the magnitude of virus replication is at a static level predetermined by the number of integrated HBV genome copies. This limitation does not exist when HBV replication in HepG2 cells is mediated by recombinant HBV baculovirus, because it is possible to modulate the level of production of HBV virions over several magnitudes simply by altering the baculovirus multiplicity of infection. In this study, the effects of 3TC on HBV replication were studied using input multiplicities of recombinant HBV baculovirus that varied over a 16 fold range. (FIG. 24, Table 5) FIG. 24 shows the effect of 0.2 $\mu$M 3TC on the HBV DNA content of medium from HepG2 cells expressing increasing levels of HBV. HepG2 cultures were infected with 25, 50, 100, 200, and 400 pfu HBV baculovirus/cell and were treated with 0.2 $\mu$M 3TC starting 24 hours p.i. Cultures were fed fresh 3TC supplemented medium daily. After 3 days of treatment (4 days p.i.). DNA was extracted from the medium of treated and untreated control cultures and analyzed by Southern Blotting. Autoradiograms shown indicate different elngths of time of exposure of the blot to film: 1 hour (A), 2 hours (B), 4 hours (C), and 8 hours (D). Relaxed circular (RC) and double-stranded (DS) forms of HBV DNA are indicated. The largest reduction of extracellular HBV DNA (>99% reduction after six days of treatment) occurred in cells infected with 25 pfu of baculovirus, the lowest multiplicity tested. Cultures infected at multiplicities ranging from 50 pfu/cell to as high as 400 pfu/cell showed an average reduction of extracellular HBV DNA of greater than 96% after six days of 3TC treatment. This finding was unexpected and clearly indicated that 0.2 $\mu$M 3TC was highly effective at inhibiting HBV replication even in the presence of large amounts of the virus. However, it is also important to note that even a 96% reduction in HBV replication still allowed high levels of HBV virions to be secreted from 3TC-treated cells which were replicating very high levels of HBV (i.e. cells infected with HBV baculovirus at a high moi).

A conclusion from these studies is that the HBV baculovirus-HepG2 system can serve as a complement to other in vitro model systems currently used for testing antiviral compounds. The results presented here agree well with previous reports of the efficacy of 3TC at reducing levels of extracellular HBV DNA in vitro. Different types of information can be obtained using the HBV baculovirus-HepG2 system because experiments can be carried out at varying levels of HBV replication including levels significantly higher than can be obtained from conventional HBV-expressing cell lines. The ability to manipulate and treat cells prior to HBV infection should also aid in studying the properties and potential efficacy of antivirals as prophylactic agents. Finally, the enhanced ability to detect HBV CCC DNA in the HBV baculovirus-HepG2 system facilitates the in vitro study of a crucial form of the HBV genome which has to be evaluated in developing any treatment protocols for curing HBV infection.

TABLE 2

Densitometric analysis of extracellular HBV DNA produced by HBV baculovirus infected HepG2 cells following treatment with increasing concentrations of 3TC.*

| | % Untreated Control[a] 3TC Concentration ($\mu$M) | | | | | |
|---|---|---|---|---|---|---|
| | 0.02 | | 0.2 | | 2.0 | |
| Days p.i.[b] | T[c] | P[d] | T | P | T | P |
| 4 | 68.1 | 69.8 | 13.4 | 10.1 | 2.4 | 1.3 |
| 7 | 39.6 | 60.6 | 5.6 | 2.4 | 2.4 | 1.2 |
| 10 | 33.0 | 38.1 | 1.9 | 0.8 | 0.8 | 0.8 |

[a]The amount of HBV DNA present in the medium of each treated culture is expressed as the percentage of the HBV DNA present in the medium of untreated cultures on the same day.
[b]Days 4, 7, and 10 p.i. correspond with 3, 6, and 9 days of 3TC treatment.
[c]Cultures treated with 3TC 24 hours after HBV-baculovirus infection are indicated by T.
[d]Cultures which received 3TC treatment starting 16 hours prior to HBV baculovirus infection (pretreatment) are indicated by P.

TABLE 3

Densitometric analysis of intracellular HBV replicative intermediates produced in HBV baculovirus infected HepG2 cells following treatment with increasing concentrations of 3TC.

| | % Untreated Control[a] 3TC Concentration ($\mu$M) | | | | | |
|---|---|---|---|---|---|---|
| | 0.02 | | 0.2 | | 2.0 | |
| Days p.i.[b] | T[c] | P[d] | T | P | T | P |
| 4 | 57.4 | 82.5 | 35.0 | 41.7 | 12.1 | 8.2 |
| 7 | 100 | 100 | 16.7 | 20.0 | 8.5 | 7.1 |
| 10 | 59.6 | 68.2 | 6.7 | 6.5 | 2.1 | 1.3 |

[a]The amount of replicative intermediates present in each treated culture is expressed as the percentage of the replicative intermediates present in untreated cultures on the same day. All sizes of DNA (SS and DS forms) were measured by densitometry.
[b]Days 4, 7, and 10 p.i. correspond with 3, 6, and 9 days of 3TC treatment.
[c]Cultures treated with 3TC 24 hours after HBV-baculovirus infection are indicated by T.
[d]Cultures which received 3TC treatment starting 16 hours prior to HBV baculovirus infection (pretreatment) are indicated by P.

TABLE 4

Densitometric analysis of non protein-associated RC HBV DNA produced by HBV baculovirus infected HepG2 cells following treatment with increasing concentrations of 3TC.[a]

| | % Untreated Control[b] 3TC Concentration ($\mu$M) | | | | | |
|---|---|---|---|---|---|---|
| | 0.02 | | 0.2 | | 2.0 | |
| Days p.i.[c] | T[d] | P[e] | T | P | T | P |
| 4 | 48.8 | 60.9 | 17.3 | 8.6 | 6.8 | 3.2 |
| 7 | 40.2 | 45.2 | 10.9 | 10.5 | 6.7 | 5.6 |

[a]Non protein-associated RC HBV DNA is present in greater quantities in HepG2 cells than CCC HBV DNA. Only RC HBV DNA was quantified by laser densitometry because of a greater signal to noise ratio verses CCC DNA.
[b]The amount of non protein-associated RC HBV DNA present in each treated culture is expressed as the percentage of the non protein-associated RC HBV DNA detected in untreated cultures on the same day.
[c]Days 4 and 7 p.i. correspond with 3 and 6 days of 3TC treatment.
[d]Cultures treated with 3TC 24 hours after HBV-baculovirus infection are indicated by T.
[e]Cultures which received 3TC treatment starting 16 hours prior to HBV baculovirus infection (pretreatment) are indicated by P.

TABLE 5

Densitometric analysis of Extracellular HBV DNA produced by HepG2 cells replicating varying levels of HBV following treatment with 0.2 $\mu$M 3TC

| | % Untreated Control[a] Moi | | | | |
|---|---|---|---|---|---|
| Days p.i.[b] | 25 | 50 | 100 | 200 | 400 |
| 4 | 4.8 | 13.9 | 27.2 | 20.7 | 18.7 |
| 7 | 0.5 | 3.5 | 3.4 | 2.2 | 4.7 |

[a]The amount of HBV DNA present in the medium of each treated culture is expressed as the percentage of the HBV DNA present in the medium of untreated cultures on the same day.
[b]Days 4 and 7 p.i. correspond with 3 and 6 days of 3TC treatment.

MATERIALS AND METHODS

Cell Culture.

Sf21 insect cells (provided by F. Boyce, Massachusetts General Hospital, Charlestown, Mass.) were maintained in Grace's insect medium supplemented with yeastolate and lactalbumin hydrolysate (Gibco BRL, Gaithersburg, Md.) in a nonhumidified incubator at 28° C. without CO2. HepG2 cells were maintained in minimal essential medium supplemented with 10% heat-inactivated fetal bovine serum (MEM-FBS). The 2.2.15 cell line (provided by B. Korba, Georgetown University, Rockville, Md.) was maintained in RPMI 1640 base supplemented with 4% fetal bovine serum. HepG2 and 2.2.15 cells were grown in humidified 37° C. incubators at 5% CO2. HepG2 cells were fed minimal essential medium (Gibco BRL, Gaithersburg, Md.) supplemented with 10% heat-inactivated fetal bovine serum.

Preparation of Baculovirus Transfer Vector.

A recombinant transfer vector was created by excising a Pstl/Sacl fragment containing the 1.3-unit length HBV construct from pTHBV1.3 (provided by H. Schaller, University of Heidelberg, Heidelberg, Germany) and cloning it into the multiple cloning region of pBlueBac4.5 (Invitrogen, Carlsbad, Calif.). Analysis of the recombinant transfer vector (pBB45HBV1.3; FIG. 1) by restriction mapping demonstrated the presence of only one copy of the HBV 1.3 construct.

Generation of Recombinant Baculoviruses Containing the 1.3 HBV Construct.

Purified pBB45HBV1.3 and linear AcMNPV baculovirus DNA were cotransfected into Sf21 cells using the BacNBlue transfection kit from Invitrogen (Carlsbad, Calif.); recombinant viruses were isolated by plaque assay according to the manufacturer's instructions. A series of recombinant viruses were amplified from isolated plaques by infecting 100-mm dishes of Sf21 cells. Viral DNA was extracted from amplified viruses as previously described. Purified viral DNA was digested with restriction enzymes and then fractionated by electrophoresis in a 1.0% agarose gel. Southern blotting was performed as described to determine which virus isolates contained the intact 1.3 HBV construct. A Boehringer Mannheim Random Prime DNA Labeling kit (Indianapolis, Ind.) was used to generate [32P]-radiolabeled probes. A full-length, double-stranded HBV genome was used as a template for all radiolabeled probes.

Preparative Baculovirus Amplification and Purification.

Baculoviruses were amplified by infecting suspension cultures of Sf21 cells in log phase at a multiplicity of infection (moi) of 0.5 pfu/cell. Infections were allowed to proceed until a majority of the cells in the flasks showed visible signs of infection (four to five days). Virions were concentrated from infected SF21 medium by centrifugation at 80,00×g and purified through a 20–60% sucrose gradient. Purified virus was titrated in Sf21 cells by end-point dilution.

Infection of HepG2 Cells with Recombinant HBV Expressing Baculovirus.

HepG2 cells were seeded at approximately 20% to 40% confluency and then were grown for 16 to 24 hours before infection. On the day of infection, duplicate plates of cells were trypsinized, and viable cell number was determined with a hemocytometer using Trypan blue exclusion. Average cell counts were calculated and used to determine the volume of high-titer viral stock necessary to infect cells at the indicated moi. Baculovirus was diluted into MEM-FBS to achieve the appropriate moi using volumes of 1.0 and 0.25 mL to infect 100-mm and 35-mm dishes, respectively. Baculovirus was adsorbed to HepG2 cells for one hour at 37° C. with gentle rocking every 15 minutes to ensure that the inoculum was evenly distributed. The inoculum was then aspirated and HepG2 cells were washed two times with phosphate-buffered saline and refed MEM-FBS.

Analysis of Secreted HBV Antigens.

Detection of hepatitis B surface antigen (HBsAg) and hepatitis B e antigen (HBeAg) was performed by radioimmunoassay using kits purchased from Abbott Laboratories (Abbott Park, ill.) and Sorin Biomedica (Saluggia, Italy), respectively. Medium from HepG2 cells was collected, centrifuged at 6,000 g to remove cellular debris, transferred to clean tubes, and stored at 20° C. until analysis. HBsAg amounts were calculated from a standard curve constructed using known amounts of HBsAg (provided with the kit). HBeAg values are expressed as fold of positive control. Medium samples were diluted appropriately so that radioimmunoassay results were within the standard curve (HBsAg) or below positive control values (HBeAg).

Analysis of Baculovirus Cytotoxicity by Determination of Lactate Dehydrogensase Release.

HepG2 cells were seeded in 24-well plates and infected one day after seeding. Medium samples exposed to infected cells were collected at 24-hour intervals and were assayed for lactate dehydrogenase (LDH) activity. Intracellular LDH activity was measured by incubating cultures in MEM-FBS containing 0.5% NP40 for 20 minutes followed by LDH determination. The percentage of extracellular LDH was calculated by dividing the LDH activity present in the medium by the total of the LDH activity obtained after the release of intracellular LDH plus the LDH activity in the medium.

Analysis of RNA.

Total RNA was isolated from HepG2 cells four days p.i. by the single-step acid guanidium method. Northern Blot analysis was performed using 20 Aig of total RNA. Hybridization was performed as described herein for Southern blotting.

Detection of Intracellular Replicative Intermediates.

HBV core particles were isolated from the cytoplasmic fraction of HepG2 cells lysed in 0.5% Np40. Cytoplasmic extracts were adjusted to 10 mmol/L MgCl2 and unprotected DNA was removed by an incubation with 500 µg/mL DNaseI for 1 hour at 37° C. Samples were then adjusted to 50 mmol/L ethylenediaminetetraacetic acid, 50 mmol/L Tris, 0.5% sodium dodecyl sulfate, and digested with 500 µg/mL. Proteinase K for 1.5 hours at 37° C. Following sequential phenol and chloroform extractions, nucleic acids were recovered by ethanol precipitation. Nucleic acids were resuspended in 50 µL TE (10 mmol/L Tris, 1 mmol/L ethylenediaminetetraacetic acid), normalized by OD260, and digested with 100 µg/mL RNase (Boehringer Mannheim, Indianapolis, Ind.) for one hour at 37° C. before analysis by electrophoresis and Southern blotting. A Molecular Dynamics (Sunnyvale, Calif.) 100A laser densitometer equipped with Quantity One software (Protein Databases Inc., Huntington Station, N.Y.) was used to analyze suitable exposures of Southern blots.

Detection of CCC DNA.

Nonprotein-bound circular HBV genomes were extracted from HepG2 cells after infection by a high salt extraction of low molecular weight DNA followed by a phenol and chloroform extraction. Nucleic acids were resuspended in 50 µL of water and normalized by OD260. All samples were treated with 100 µg/mL RNase and 30 U of Plasmid-Safe ATP-Dependent DNase (Epicenter Technologies, Madison, Wis.). After a two-hour incubation at 37° C., Plasmid-Safe DNase was heat inactivated at 65° C. according to the manufacturer's instructions. Each sample was separated into two aliquots and one aliquot was digested with XhoI for one hour at 37° C. Samples were analyzed by electrophoresis and Southern blotting.

Extracellular HBV DNA Analysis.

Conditioned medium was collected from HepG2 cells and subjected to centrifugation at 6,000 g for 5 minutes to I5-remove cellular debris. HBV particles were precipitated with 10% PEG 8000 and were concentrated by centrifugation at 12,000×g. Viral pellets were resuspended in 1 mL of MEM-FBS and divided into two aliquots. One set of aliquots was treated with 750 µg/mL Pronase for one hour and then with 500 mg/mL DNase 1 for one hour. Both sets of aliquots were then digested with Proteinase K, and extracted with phenol and chloroform. DNA was precipitated with 0.1 volume of 3 mol/L sodium acetate and 1 volume of isopropanol. Ten micrograms of transfer RNA was added as a carrier during precipitation. Pellets were resuspended in 25 µL of TE and digested with 0.5 mg/mL RNase for 1 hour. DNA was then analyzed by electrophoresis and Southern blotting.

Cesium Chloride Gradient Analysis of Extracellular Viral Particles.

Medium from HBV baculovirus infected HepG2 cells was collected and subjected to centrifugation for ten minutes at 10,000 g and filtration through a 0.45-nm filter (Gelman Sciences, Ann Arbor, Mich.) to remove cellular debris. 3.0 g of CsCl (Boehringer Mannheim, Indianapolis, Ind.) were dissolved into 9 mL of clarified medium and subjected to centrifugation at 200,000 g for 75 hours. Seventeen fractions of approximately 0.6 mL were collected from the gradient following centrifugation. The density of each fraction was determined by refractometry. HBsAg content of fractions was measured by radioimmunoassay. Selected fractions were desalted by repeated dilution in water followed by concentration using Centricon ten concentrators (Amicon Inc., Beverly, Mass.). DNA was extracted from desalted fractions by Proteinase K digestion followed by phenol and chloroform extraction and ethanol precipitation.

Immunohistochemical Analysis.

HepG2 cells were fixed in zinc formalin for five minutes approximately 36 hours p.i. Hepatitis B core antigen (HBcAg) staining was carried out using rabbit anti-HBcAg from Dako (Carpinteria, Calif.) at a dilution of 1:700. An equal dilution of rabbit serum was used as a negative control. Immunoperoxidase detection of the primary antibodies was carried out using a Vectastain ABC kit (Vector Laboratories, Burlingame, Calif.) according to the manufacturer's instructions. Cells were counterstained with hematoxylin (Shandon Lipshaw, Pittsburgh, Pa.) before microscopic examination.

TC Treatment.

3TC was a gift of BioChem Therapeutic Inc. (Laval, Quebec, Canada). 3TC was resuspended in sterile water, aliquoted, and frozen at −20° C. to avoid repeated freezing and thawing of the drug. Medium containing 3TC was prepared daily as needed using fresh aliquots of 3TC. In experiments in which 3TC treatment was initiated after viral infection, HepG2 cells were exposed to the indicated concentration of 3TC 24 hours post infection (p.i.) with HBV baculovirus. In experiments utilizing pretreatment with 3TC, cells were fed medium containing 3TC 16 hours prior to HBV baculovirus infection, HBV baculovirus infection was also carried out in medium containing 3TC, and cells were refed fresh medium containing 3TC immediately after completion the infection and washing procedures.

DOCUMENTS CITED

Boyce F M, Bucher N L. Baculovirus-mediated gene transfer into mammalian cells. Proc Nat Acad Sci 1996; 93: 2348–2352.

Doong S L, Tsai C H, Schinazi R F, Liotta D C, Cheng Y C. Inhibition of the replication of hepatitis B virus in vitro by 2',3'-dideoxy-3'-thiacytidine and related analogues. Proc Nat Acad Sci 1991; 88:8495–8499.

Guidotti L G, Matzke B, Schaller H, Chisari F V. High-level hepatitis B virus replication in transgenic mice. J Virol 1995; 69: 6158–6169.

Hofmann C, Sandig V, Jennings G, Rudolph M, Schiag P, Strauss M. Efficient gene transfer into human hepatocytes by baculovirus vectors. Proc Nat Acad Sci 1995; 92:10099–10103.

Knowles B B, Howe C C, Aden D P. Human hepatocellular carcinoma cell lines secrete the major plasma proteins and hepatitis B surface antigen. Science 1980; 209:497–499.

Korba B E, Gerin J L. Use of a standardized cell culture assay to assess activities of nucleoside analogs against hepatitis B virus replication. Antiviral Res 1992; 19:55–70.

Kruining J, Heijtink R A, Schalm S W. Antiviral agents in hepatitis B virus transfected cell lines: inhibitory and cytotoxic effect related to time of treatment. Journal of Hepatology 1995; 22:263–267.

Moraleda G, Saputelli J, Aldrich C E, Averett D, Condreay L, Mason W S. Lack of effect of antiviral therapy in nondividing hepatocyte cultures on the closed circular DNA of woodchuck hepatitis virus. J Virol 1997; 71:9392–35 9399.

Nakabayashi H, Taketa K, Miyano K, Yamane T, Sato J. Growth of human hepatoma cells lines with differentiated functions in chemically defined medium. Cancer Research 1982; 42:3858–3863.

Sandig V, Hofmann C, Steinert S, Jennings G, Schlag P, Strauss M. Gene transfer into hepatocytes and human liver tissue by baculovirus vectors. Hum Gene Ther 1996; 7: 1937–1945.

Sells M A, Chen M L, Acs G. Production of hepatitis B virus particles in Hep G2 cells transfected with cloned hepatitis B virus DNA. Proc Nat Acad Sci 1987; 84:1005–1009.

Sells M A, Zelent A Z, Shvartsman M, Acs G. Replicative intermediates of 50 hepatitis B virus in HepG2 cells that produce infectious virions. J Virol 1988; 62:2836–2844.

What is claimed is:

1. A method for selecting a candidate agent to reduce hepatitis B virus expression in human cells, said method comprising:

(a) infecting the cells with a genetic construct comprising at least a part of a baculovirus genome and at least a full length hepatitis B virus genome such that it is replication competent;

(b) contacting the infected cells with the candidate agent;

(c) determining whether there is less expression of the hepatitis virus in the contacted cells than in an infected cell that is not contacted with the candidate agent; and (d) selecting the candidate agent if there is less expression.

2. The method of claim 1 wherein the agent is lamivudine.

3. The method of claim 1, wherein the cells are from the cell line HepG2.

4. The method of claim 1, wherein the cells are from the cell line Huh-7.

5. The method of claim 1, wherein the candidate agent is an antiviral agent.

6. The method of claim 1, wherein the candidate agent is a cytokine.

7. A hepatic cell infected with a genetic construct comprising at least a part of a baculovirus genome and at least a full length HBV genome such that HBV replication can occur.

8. The hepatic cell of claim 7, wherein the cell is from the cell line HepG2.

9. The hepatic cell of claim 7, wherein the cell is from the cell line Huh-7.

10. The hepatic cell of claim 7, wherein the HBV virus genome that is in the genetic construct is a 1.3-genome length HBV construct which is capable of driving high levels of HBV replication.

11. A method for high-level transient delivery and expression of a desired nucleotide sequence from HBV to a cell of hepatic origin, said method comprising:

(a) constructing a vector containing:
    (i) an HBV promoter;
    (ii) an HBV enhancer;
    (iii) a desired HBV sequence; and
    (iv) a part of a baculovirus genome; and (b) infecting cells of hepatic origin with said vector.

* * * * *